(12) United States Patent
Cheresh et al.

(10) Patent No.: US 11,052,089 B2
(45) Date of Patent: Jul. 6, 2021

(54) METHODS FOR INHIBITING ALPHA-V BETA-3 EXPRESSION ON CANCER STEM CELLS AND INHIBITING PROGRESSION TO A CANCER STEM CELL PHENOTYPE

(71) Applicant: The Regents of the University of California, Oakland, CA (US)

(72) Inventors: David A. Cheresh, La Jolla, CA (US); Maricel Gozo, La Jolla, CA (US); Mayra Yebra, La Jolla, CA (US); Laetitia Seguin, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 113 days.

(21) Appl. No.: 15/537,403

(22) PCT Filed: Dec. 18, 2015

(86) PCT No.: PCT/US2015/066762
§ 371 (c)(1),
(2) Date: Jun. 16, 2017

(87) PCT Pub. No.: WO2016/100858
PCT Pub. Date: Jun. 23, 2016

(65) Prior Publication Data
US 2018/0000821 A1    Jan. 4, 2018

Related U.S. Application Data

(60) Provisional application No. 62/148,136, filed on Apr. 15, 2015, provisional application No. 62/094,020, filed on Dec. 18, 2014.

(51) Int. Cl.
| | |
|---|---|
| *A61P 35/00* | (2006.01) |
| *A61P 35/04* | (2006.01) |
| *A61K 31/506* | (2006.01) |
| *A61K 31/517* | (2006.01) |
| *G01N 33/574* | (2006.01) |
| *A61K 45/06* | (2006.01) |
| *A61K 31/454* | (2006.01) |
| *A61K 31/444* | (2006.01) |

(52) U.S. Cl.
CPC .......... *A61K 31/517* (2013.01); *A61K 31/444* (2013.01); *A61K 31/454* (2013.01); *A61K 45/06* (2013.01); *G01N 33/574* (2013.01)

(58) Field of Classification Search
CPC ......... A61K 8/36; A61K 31/506; A61P 35/00; A61P 35/04
See application file for complete search history.

(56) References Cited

U.S. PATENT DOCUMENTS

| | | | |
|---|---|---|---|
| 8,338,638 B2 | 12/2012 | Achanath et al. | |
| 2006/0167107 A1 | 7/2006 | Kundu et al. | |
| 2008/0226760 A1* | 9/2008 | Torrent Campmany | A61K 36/22 424/776 |
| 2012/0178757 A1* | 7/2012 | Powe | A61K 31/135 514/236.2 |
| 2013/0196933 A1 | 8/2013 | Raychaudhuri et al. | |
| 2014/0154264 A1 | 6/2014 | Cheresh et al. | |
| 2016/0101076 A1 | 4/2016 | Weigel | |

OTHER PUBLICATIONS

Mittelbronn et al. ( Histology and Histopathology, 28(6):749-758) (Year: 2013).*
Omanakuttan et al. (Molecular Pharmacology Fast Forward. Published on Jun. 28, 2012 as DOI: 10.1124/mol.112.079020) (Year: 2012).*
Seong et al. ((2013). Anacardic acid induces mitochondrial-mediated apoptosis in the A549 human lung adenocarcinoma cells. International Journal of Oncology, 42, 1045-1051). (Year: 2013).*
Desgroselher et al., "Integrin alpha-v beta-3 Drives Slug Activation and Sternness in the Pregnant and Neoplastic Mammary Gland" Developmental Cell, Aug. 11, 2014, v 30, p. 295-308.
Desgroselher et al., "An integrin αvβ3-c-Src oncogenic unit promotes anchorage-independence and tumor progression" Nature Medicine, Oct. 2009, v 15, n. 10, p. 1163-1170.
Kubo et al., "Structure-Antibacterial activity relationships of anacardic acids" J. Agric. Food Chem., 1993, v 41, p. 1016-1019.
Seguin et al., "A β3 integrin-KRAS-RalB complex drives tumor sternness and resistance to EGFR inhibition" Nat Cell Biol. May 2014, v 16, n. 5, p. 457-468.
Thomas, Shane, et al., "Notification of Transmittal of the International Search Report and the Written Opinion of the International Searching Authority, or the Declaration", Patent Cooperation Treaty Application No. PCT/US2015/066762, United States of America as International Searching Authority, Date of Completion of International Search Feb. 25, 2016, Date of mailing of International Search Report dated Mar. 4, 2016, 10 pages.

* cited by examiner

*Primary Examiner* — Jeffrey S Lundgren
*Assistant Examiner* — Chris E Simmons
(74) *Attorney, Agent, or Firm* — Greer Burns & Crain, Ltd.; Gregory P. Einhorn

(57) ABSTRACT

In alternative embodiments, provided are compositions and methods for treating, enhancing the drug sensitivity of, and preventing the formation of cancer stems cells, including preventing or slowing the development or generation of a beta-3 (β3)-expressing, or integrin β3 (ITG-B3)-expressing cancer or tumor cells. In alternative embodiments, provided are methods using histone acetyl transferase inhibitors and/or histone methyl transferase inhibitors to determine therapeutic values in cancer cells that induce an integrin β3 (ITGB3) polypeptide expression. In alternative embodiments, provided are kits, blister packages, lidded blisters or a blister card or packet, clamshells, trays or shrink wraps, comprising at least one compound, composition or formulation used to practice a method as provided herein, and at least one Growth Factor Inhibitor.

5 Claims, 16 Drawing Sheets

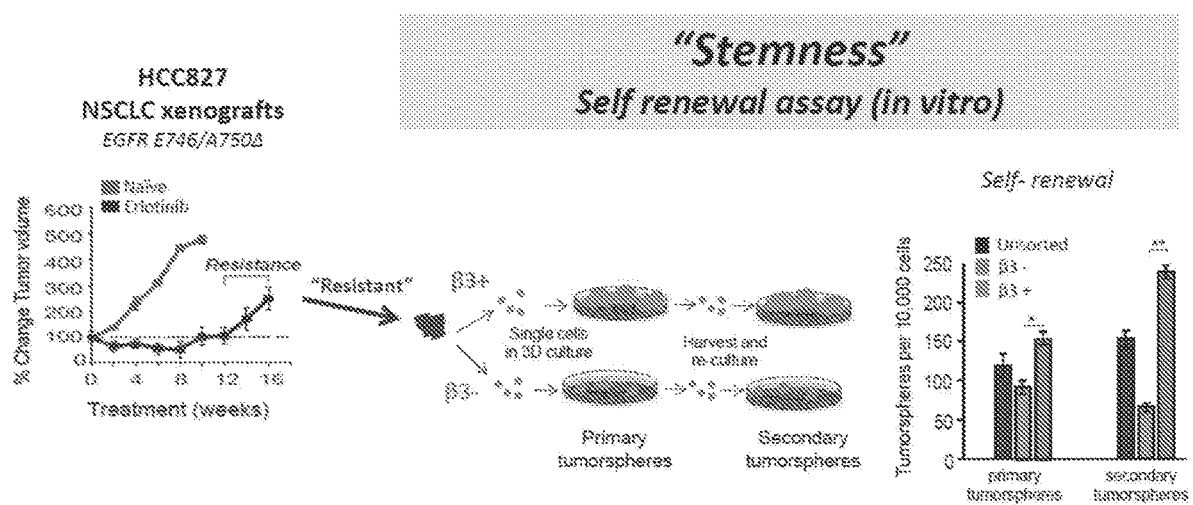
Fig. 4A                    Fig. 4B                    Fig. 4C

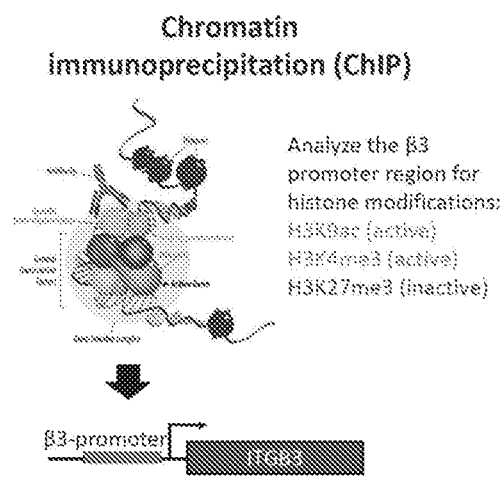
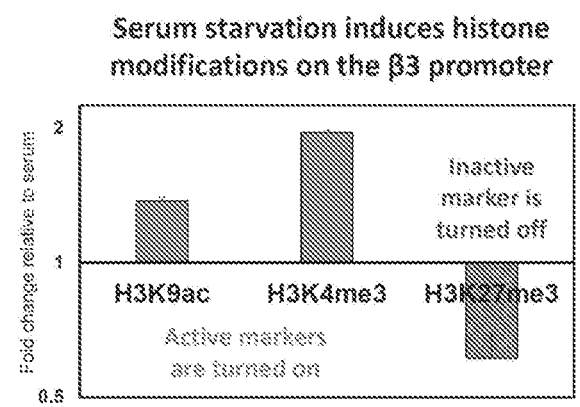
Fig. 10A
Fig. 10B

US 11,052,089 B2

METHODS FOR INHIBITING ALPHA-V BETA-3 EXPRESSION ON CANCER STEM CELLS AND INHIBITING PROGRESSION TO A CANCER STEM CELL PHENOTYPE

RELATED APPLICATIONS

This application is a national phase of International patent application serial number PCT/US2015/066762, filed Dec. 18, 2015, which claims benefit of priority to U.S. provisional application 62/094,020, filed Dec. 18, 2014 and U.S. provisional application 62/148,136, filed Apr. 15, 2015. The contents of each of these applications are incorporated herein by reference in their entirety and for all purposes.

GOVERNMENT RIGHTS

This invention was made with government support under grant numbers CA45726, CA168692, HL57900, R37-50286, CA155620; awarded by the National Institutes of Health (NIH). The government has certain rights in the invention.

TECHNICAL FIELD

This invention generally relates to cell and molecular biology, diagnostics and oncology. In alternative embodiments, provided are compositions and methods for treating, enhancing the drug sensitivity of, and preventing the formation of cancer stems cells, including preventing or slowing the development or generation of a beta-3 (β3)-expressing, or integrin β3 (ITGB3)-expressing cancer or tumor cells. In alternative embodiments, provided are methods using histone acetyl transferase (HAT) inhibitors (e.g., anacardic acid, or 2-hydroxy-6-[(8Z,11Z)-pentadeca-8,11,14-trienyl]benzoic acid; cyclopentylidene-[4-(4-chlorophenyl)thiazol-2-yl)hydrazone; or (E,E)-1,7-bis(4-Hydroxy-3-methoxyphenyl)-1,6-heptadiene-3,5-dione, diferuloylmethane or diferulylmethane; or (2R,3 S)-rel-4-Methylene-5-oxo-2-propyltetrahydrofuran-3-carboxylic acid), to determine therapeutic values in cancer cells that induce an integrin β3 (ITGB3) polypeptide expression.

In alternative embodiments, provided are compositions and methods for treating, enhancing the drug sensitivity of, and preventing the formation of cancer stems cells, including preventing or slowing the development or generation of a beta-3 (β3)-expressing, or integrin β3 (ITGB3)-expressing cancer or tumor cells. In alternative embodiments, provided are methods using histone methyl transferase inhibitors to determine therapeutic values in cancer cells that induce an integrin β3 (ITGB3) polypeptide expression.

BACKGROUND

Histone acetyltransferases (HATs) are enzymes that acetylate conserved lysine amino acids on histone proteins by transferring an acetyl group from acetyl CoA to form ε-N-acetyllysine. By transferring an acetyl group to the histones, genes can be turned on and off. Histone acetylation increases gene expression. Acetylation is generally associated with elevated transcription, while deacetylated histones are often associated with gene repression. Histone methyltransferases (HMT) are histone-modifying enzymes, (including histone-lysine N-methyltransferase and histone-arginine N-methyltransferase), that catalyze the transfer of one, two, or three methyl groups to lysine and arginine residues of histone proteins. Methylation of histones is important biologically because it is the principal epigenetic modification of chromatin that determines gene expression, genomic stability, stem cell maturation, cell lineage development, genetic imprinting, DNA methylation, and cell mitosis Research has suggested that deregulation of histone methylation plays a role in human carcinogenesis. For example, JARID1A/B demethylases have been shown to play a role in tumor formation, metastasis and drug resistance, and therefore may be targets for cancer treatment. Histone-lysine N-methyltransferase EZH2 small molecule inhibitors have been shown to work as targeted therapeutics for subsets of human cancers bearing defined genetic lesions, such as non-Hodgkin's lymphomas with EZH2 gain-of-function mutations and other tumor types with loss of INI1 function. Small molecule inhibitors of the histone H3 lysine 27 (H3K27)-specific methyltransferase Enhancer of Zeste Homolog 2 (EZH2) have been shown to cause selective cell killing of Non Hodgkin Lymphoma cell lines and regression in subcutaneous NHL models in vivo. Inhibitors of histone demethylase LSD1 have been shown to selectively abrogate the clonogenic potential of acute myeloid leukemia cells with MLL translocations, sparing the repopulating potential of normal hematopoietic stem cells, and to reduce leukemic stem cell potential, overcome the differentiation block in AML cell lines, and induce apoptosis/inhibit proliferation in AML cell lines.

SUMMARY

Acetyl Transferase Inhibitors
  In alternative embodiments, provided are methods for:
    preventing or slowing the development or generation of a beta-3 (β3)-expressing, or integrin β3 (ITGB3)-expressing, cancer cell or tumor cell, or preventing or slowing the development of an alpha-V (α-5)/beta-3 (β3)-expressing cancer cell or tumor cell, or for preventing or slowing the phenotypic conversion of a cancer cell or tumor cell not expressing a beta-3 (β3), or integrin β3 (ITGB3), polypeptide to a cancer cell or tumor cell that expresses a beta-3 (β3), or integrin β3 (ITGB3), polypeptide, or for preventing or slowing the phenotypic conversion of a cancer cell or tumor cell not expressing an alpha-V (α-5)/beta-3 (β3) polypeptide dimer to a cancer cell or tumor cell that expresses an alpha-V (α-5)/beta-3 (β3) polypeptide dimer;
    overcoming or diminishing or preventing a conversion of a cancer cell to a cancer stem cell, or acquiring a "stemness" phenotype; or, reversing, diminishing or preventing phenotypic conversion of a cancer cell to a cancer stem cell or a cancer cell having a "stemness" phenotype;
    overcoming or diminishing or preventing a Growth Factor Inhibitor (GFI) resistance in a cell;
    overcoming or diminishing or preventing tumor progression or metastasis of a cancer cell;
    sensitizing, increasing sensitivity to or re-sensitizing a cancer stem cell (e.g., a drug resistant cancer stem cell) or a tumor stem cell (e.g., a drug resistant tumor stem cell) to a cancer therapy, or making a cancer stem cell (e.g., a drug resistant cancer stem cell) or a tumor stem cell (e.g., a drug resistant tumor stem cell) more sensitive to a cancer therapy (making the cancer therapy more effective),
      wherein optionally the cancer therapy is a drug therapy or a radiation therapy, and optionally the drug therapy is a receptor tyrosine kinase (RTK) inhibitor therapy (sensitizing, increasing sensitivity to or re-sensitizing a cancer stem cell or a tumor stem cell to a Receptor Tyrosine Kinase (RTK) inhibitor therapy);

sensitizing, increasing sensitivity to or re-sensitizing a dysfunctional cell, a tumor or cancer to a drug, wherein optionally the drug is a Receptor Tyrosine Kinase (RTK) inhibitor, an EGFR1 inhibitor, an EGFR1/EGFR2 inhibitor or an IGF-1R inhibitor, or an erlotinib, a linsitinib, a lapatinib or a lenalidomide;

sensitizing, increasing sensitivity to or re-sensitizing a tumor that is resistant to a cancer or anti-tumor drug, or reversing a tumor cell, a cancer cell, a cancer stem cell or a dysfunctional cell initiation or self-renewal capacity, wherein optionally the cell is a tumor cell, a cancer cell, a cancer stem cell, or a dysfunctional cell, the method comprising:

administering at least one compound, composition or formulation comprising or consisting of:

(i) an inhibitor or depleter of an acetyl transferase gene, transcript (message) and/or inhibitor of an acetyl transferase protein expression or activity (e.g., anacardic acid, or 2-hydroxy-6-[(8Z,11Z)-pentadeca-8,11,14-trienyl]benzoic acid; cyclopentylidene-[4-(4-chlorophenyl)thiazol-2-yl)hydrazone; or (E,E)-1,7-bis(4-Hydroxy-3-methoxyphenyl)-1,6-heptadiene-3,5-dione, diferuloylmethane or diferulylmethane; or (2R,3S)-rel-4-Methylene-5-oxo-2-propyltetrahydrofuran-3-carboxylic acid); or, a compound, composition or formulation that reduces or inhibits acetyl transferase gene, transcript (message) and/or an acetyl transferase protein expression or activity, (ii) an inhibitor of an acetyl transferase pathway, wherein optionally the acetyl transferase is a histone acetyl transferase.

In alternative embodiments, any combination of an inhibitor or depleter of an acetyl transferase gene, transcript (message) and/or inhibitor of an acetyl transferase protein expression or activity and/or an inhibitor or depleter of a methyl transferase gene, transcript (message) and/or inhibitor of an acetyl transferase protein expression or activity are used to practice the methods of compositions as provided herein.

In alternative embodiments, provided are methods wherein the drug therapy is a receptor tyrosine kinase (RTK) inhibitor therapy, and inhibition or depletion of acetyl transferase gene, transcript (message) and/or protein expression or activity sensitizes, increases sensitivity to or re-sensitizes a cancer stem cell or a tumor stem cell to a Receptor Tyrosine Kinase (RTK) inhibitor therapy.

In alternative embodiments of the methods, the drug therapy is or comprises or further comprises administration of at least one growth factor inhibitor, which optionally comprises a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor;

wherein optionally the combination or the therapeutic combination comprises: (i) an inhibitor or depleter of a Src or a Tank Binding Kinase-1 (TBK1) protein or an inhibitor of Src or TBK1 protein activation, wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™, and (ii) an RTK inhibitor, wherein optionally the RTK inhibitor is a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor or a combination thereof.

In alternative embodiments of the methods:

(a) the at least one compound, composition or formulation, or combination of compounds, is formulated as a pharmaceutical composition;

(b) the method of (a), wherein the compound, composition or formulation or pharmaceutical composition is administered in vitro, ex vivo or in vivo, or is administered to an individual in need thereof;

(c) the method of (a) or (b), wherein the at least one compound, composition or formulation is a pharmaceutical composition is formulated for administration intravenously (IV), parenterally, nasally, topically, orally, or by liposome or targeted or vessel-targeted nanoparticle delivery;

(d) the method of any of (a) to (c), wherein the compound or composition comprises or is an inhibitor of transcription, translation or protein expression;

(e) the method of any of (a) to (d), wherein the compound or composition is a small molecule, a protein, an antibody, a monoclonal antibody, a nucleic acid, a lipid or a fat, a polysaccharide, an RNA or a DNA;

(f) the method of any of (a) to (e), wherein the compound or composition further comprises, or the method further comprises administration of: a VITAXIN™ (Applied Molecular Evolution, San Diego, Calif.) antibody, a humanized version of an LM609 monoclonal antibody, an LM609 monoclonal antibody, or any antibody that functionally blocks an $\alpha_v\beta_3$ integrin or any member of an $\alpha_v\beta_3$ integrin-comprising complex or an integrin $\alpha_v\beta_3$ (anb3)/RalB/NFkB signaling axis;

(g) the method of any of (a) to (e), wherein the compound or composition further comprises, or the method further comprises administration of, a Src inhibitor, a dasatinib, a saracatinib; a bosutinib; a NVP-BHG712, or any combination thereof;

(h) the method of any of (a) to (g), wherein the compound or composition further comprises, or the method further comprises administration of, a Growth Factor Inhibitor, an anti-metabolite inhibitor, a gemcitabine, GEMZAR™, a mitotic poison, a paclitaxel, a taxol, ABRAXANE™, an erlotinib, TARCEVA™, a lapatinib, TYKERB™, or an insulin growth factor inhibitor, or any combination thereof.

In alternative embodiments, provided are kits, blister packages, lidded blisters or a blister card or packet, clamshells, trays or shrink wraps, comprising;

(a) (i) at least one compound, composition or formulation used to practice a method as provided herein (e.g., a histone acetyl transferase inhibitor), and (ii); at least one Growth Factor Inhibitor, wherein optionally the Growth Factor Inhibitor is or comprises an anti-metabolite inhibitor, a gemcitabine, GEMZAR™, a mitotic poison, a paclitaxel, a taxol, ABRAXANE™, an erlotinib, TARCEVA™, a lapatinib, TYKERB™, or an insulin growth factor inhibitor, or any combination thereof; or, the Growth Factor Inhibitor decreases, slows or blocks new blood vessel growth, neovascularization or angiogenesis; or, wherein administering the Growth Factor Inhibitor treats or ameliorates conditions that are responsive to blocking or slowing cell growth, and/or the development of neovascularization or new blood vessels; or (b) the kit of (a), further comprising instructions for practicing a method as provided herein, wherein optionally the kit, blister package, lidded blister, blister card, packet, clamshell, tray or shrink wrap comprises: an erlotinib with either Lenalidomide or PS-1145, or Lenalidomide and PS-1145.

In alternative embodiments, provided are methods for determining the therapeutic value of a drug in treating a beta-3 (β3)-expressing, or integrin β3 (ITGB3)-expressing, cancer cell or tumor cell, wherein optionally the therapeutic value comprises the property or value of whether an individual or a patient would benefit from or respond to administration of the drug, or which individuals or patients would benefit from a combinatorial approach comprising administration of a combination of: at least one growth factor and at least one compound, composition or formulation used to practice a method as provided herein, the method comprising:

(a) (i) administering at least one compound, composition or formulation comprising or consisting of: an inhibitor or depleter of an acetyl transferase gene, transcript (message) and/or acetyl transferase protein expression or activity (e.g., anacardic acid, or 2-hydroxy-6-[(8Z,11Z)-pentadeca-8,11,14-trienyl]benzoic acid; cyclopentylidene-[4-(4-chlorophenyl)thiazol-2-yl]hydrazone; or (E,E)-1,7-bis(4-Hydroxy-3-methoxyphenyl)-1,6-heptadiene-3,5-dione, diferuloylmethane or diferulylmethane; or (2R,3 S)-rel-4-Methylene-5-oxo-2-propyltetrahydrofuran-3-carboxylic acid); or, a compound, composition or formulation that reduces or inhibits acetyl transferase gene, transcript (message) and/or acetyl transferase protein expression or activity, wherein optionally the acetyl transferase is a histone acetyl transferase;

(ii) administering the drug whose therapeutic value is to be determined, wherein optionally step (a)(i) is performed before step (a)(ii), or step (a)(ii) is performed before step (a)(i), step (a)(i) is performed with or about the same time as step (a)(ii); and (b) determining the therapeutic value of the drug in treating a beta-3 (β3)-expressing, or integrin β3 (ITGB3)-expressing, cancer cell or tumor cell.

In alternative embodiments, provided are Uses of a compound, composition or formulation in the manufacture of a medicament for:

preventing or slowing the development or generation of a beta-3 (β3)-expressing, or integrin β3 (ITGB3)-expressing, cancer cell or tumor cell, or preventing or slowing the development of an alpha-V (α-5)/beta-3 (β3)-expressing cancer cell or tumor cell, or for preventing or slowing the phenotypic conversion of a cancer cell or tumor cell not expressing a beta-3 (β3), or integrin β3 (ITGB3), polypeptide to a cancer cell or tumor cell that expresses a beta-3 (β3), or integrin β3 (ITGB3), polypeptide, or for preventing or slowing the phenotypic conversion of a cancer cell or tumor cell not expressing an alpha-V (α-5)/beta-3 (β3) polypeptide dimer to a cancer cell or tumor cell that expresses an alpha-V (α-5)/beta-3 (β3) polypeptide dimer;

overcoming or diminishing or preventing a conversion of a cancer cell to a cancer stem cell, or acquiring a "stemness" phenotype; or, reversing, diminishing or preventing phenotypic conversion of a cancer cell to a cancer stem cell or a cancer cell having a "stemness" phenotype;

overcoming or diminishing or preventing a Growth Factor Inhibitor (GFI) resistance in a cell;

overcoming or diminishing or preventing tumor progression or metastasis of a cancer cell;

sensitizing, increasing sensitivity to or re-sensitizing a cancer stem cell (e.g., a drug resistant cancer stem cell) or a tumor stem cell (e.g., a drug resistant tumor stem cell) to a cancer therapy, or making a cancer stem cell (e.g., a drug resistant cancer stem cell) or a tumor stem cell (e.g., a drug resistant tumor stem cell) more sensitive to a cancer therapy (making the cancer therapy more effective), wherein optionally the cancer therapy is a drug therapy or a radiation therapy, and optionally the drug therapy is a receptor tyrosine kinase (RTK) inhibitor therapy (sensitizing, increasing sensitivity to or re-sensitizing a cancer stem cell or a tumor stem cell to a Receptor Tyrosine Kinase (RTK) inhibitor therapy);

sensitizing, increasing sensitivity to or re-sensitizing a dysfunctional cell, a tumor or cancer to a drug, wherein optionally the drug is a Receptor Tyrosine Kinase (RTK) inhibitor, an EGFR1 inhibitor, an EGFR1/EGFR2 inhibitor or an IGF-1R inhibitor, or an erlotinib, a linsitinib, a lapatinib or a lenalidomide;

sensitizing, increasing sensitivity to or re-sensitizing a tumor that is resistant to a cancer or anti-tumor drug, or reversing a tumor cell, a cancer cell, a cancer stem cell or a dysfunctional cell initiation or self-renewal capacity, wherein optionally the cell is a tumor cell, a cancer cell, a cancer stem cell, or a dysfunctional cell, wherein the compound, composition or formulation comprises or consists of: an inhibitor or depleter of an acetyl transferase gene, transcript (message) and/or protein expression or activity; or, a compound, composition or formulation that reduces or inhibits acetyl transferase gene, transcript (message) and/or protein expression or activity, wherein optionally the acetyl transferase is a histone acetyl transferase.

In alternative embodiments, provided are combinations, or therapeutic combinations, for:

preventing or slowing the development or generation of a beta-3 (β3)-expressing, or integrin β3 (ITGB3)-expressing, cancer cell or tumor cell, or preventing or slowing the development of an alpha-V (α-5)/beta-3 (β3)-expressing cancer cell or tumor cell, or for preventing or slowing the phenotypic conversion of a cancer cell or tumor cell not expressing a beta-3 (β3), or integrin β3 (ITGB3), polypeptide to a cancer cell or tumor cell that expresses a beta-3 (β3), or integrin β3 (ITGB3), polypeptide, or for preventing or slowing the phenotypic conversion of a cancer cell or tumor cell not expressing an alpha-V (α-5)/beta-3 (β3) polypeptide dimer to a cancer cell or tumor cell that expresses an alpha-V (α-5)/beta-3 (β3) polypeptide dimer;

overcoming or diminishing or preventing a conversion of a cancer cell to a cancer stem cell, or acquiring a "stemness" phenotype; or, reversing, diminishing or preventing phenotypic conversion of a cancer cell to a cancer stem cell or a cancer cell having a "stemness" phenotype;

overcoming or diminishing or preventing a Growth Factor Inhibitor (GFI) resistance in a cell;

overcoming or diminishing or preventing tumor progression or metastasis of a cancer cell;

sensitizing, increasing sensitivity to or re-sensitizing a cancer stem cell (e.g., a drug resistant cancer stem cell) or a tumor stem cell (e.g., a drug resistant tumor stem cell) to a cancer therapy, or making a cancer stem cell (e.g., a drug resistant cancer stem cell) or a tumor stem cell (e.g., a drug resistant tumor stem cell) more sensitive to a cancer therapy (making the cancer therapy more effective), wherein optionally the cancer therapy is a drug therapy or a radiation therapy, and optionally the drug therapy is a receptor tyrosine kinase (RTK) inhibitor therapy (sensitizing, increasing sensitivity to or re-sensitizing a cancer stem cell or a tumor stem cell to a Receptor Tyrosine Kinase (RTK) inhibitor therapy);

sensitizing, increasing sensitivity to or re-sensitizing a dysfunctional cell, a tumor or cancer to a drug, wherein optionally the drug is a Receptor Tyrosine Kinase (RTK) inhibitor, an EGFR1 inhibitor, an EGFR1/EGFR2 inhibitor or an IGF-1R inhibitor, or an erlotinib, a linsitinib, a lapatinib or a lenalidomide;

sensitizing, increasing sensitivity to or re-sensitizing a tumor that is resistant to a cancer or anti-tumor drug, or reversing a tumor cell, a cancer cell, a cancer stem cell or a dysfunctional cell initiation or self-renewal capacity, wherein optionally the cell is a tumor cell, a cancer cell, a cancer stem cell, or a dysfunctional cell, wherein the combination comprises or consists of:

(a) a compound, composition or formulation comprises or consists of: an inhibitor or depleter of an acetyl transferase gene, transcript (message) and/or protein expression or activity; or, a compound, composition or formulation that reduces or inhibits acetyl transferase gene, transcript (message) and/or protein expression or activity, wherein optionally the acetyl transferase is a histone acetyl transferase; and (b) a growth factor inhibitor, optionally comprising a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor.

Methyl Transferase Inhibitors

In alternative embodiments, provided are methods for:

preventing or slowing the development or generation of a beta-3 (β3)-expressing, or integrin β3 (ITGB3)-expressing, cancer cell or tumor cell, or preventing or slowing the development of an alpha-V (α-5)/beta-3 (β3)-expressing cancer cell or tumor cell, or for preventing or slowing the phenotypic conversion of a cancer cell or tumor cell not expressing a beta-3 (β3), or integrin β3 (ITGB3), polypeptide to a cancer cell or tumor cell that expresses a beta-3 (β3), or integrin β3 (ITGB3), polypeptide, or for preventing or slowing the phenotypic conversion of a cancer cell or tumor cell not expressing an alpha-V (α-5)/beta-3 (β3) polypeptide dimer to a cancer cell or tumor cell that expresses an alpha-V (α-5)/beta-3 (β3) polypeptide dimer;

overcoming or diminishing or preventing a conversion of a cancer cell to a cancer stem cell, or acquiring a "stemness" phenotype; or, reversing, diminishing or preventing phenotypic conversion of a cancer cell to a cancer stem cell or a cancer cell having a "stemness" phenotype;

overcoming or diminishing or preventing a Growth Factor Inhibitor (GFI) resistance in a cell;

overcoming or diminishing or preventing tumor progression or metastasis of a cancer cell;

sensitizing, increasing sensitivity to or re-sensitizing a cancer stem cell or a tumor stem cell to a cancer therapy, or making a cancer stem cell or a tumor stem cell more sensitive to a cancer therapy (making the cancer therapy more effective), wherein optionally the cancer therapy is a drug therapy or a radiation therapy, and optionally the drug therapy is a receptor tyrosine kinase (RTK) inhibitor therapy (sensitizing, increasing sensitivity to or re-sensitizing a cancer stem cell or a tumor stem cell to a Receptor Tyrosine Kinase (RTK) inhibitor therapy);

sensitizing, increasing sensitivity to or re-sensitizing a dysfunctional cell, a tumor or cancer to a drug, wherein optionally the drug is a Receptor Tyrosine Kinase (RTK) inhibitor, an EGFR1 inhibitor, an EGFR1/EGFR2 inhibitor or an IGF-1R inhibitor, or an erlotinib, a linsitinib, a lapatinib or a lenalidomide;

sensitizing, increasing sensitivity to or re-sensitizing a tumor that is resistant to a cancer or anti-tumor drug, or reversing a tumor cell, a cancer cell, a cancer stem cell or a dysfunctional cell initiation or self-renewal capacity, wherein optionally the cell is a tumor cell, a cancer cell, a cancer stem cell, or a dysfunctional cell, the method comprising:

administering at least one compound, composition or formulation comprising or consisting of:

(iii) an inhibitor or depleter of a methyl transferase gene, transcript (message) and/or protein expression or activity; or, a compound, composition or formulation that reduces or inhibits methyl transferase gene, transcript (message) and/or protein expression or activity, (iv) an inhibitor of a methyl transferase pathway wherein optionally the methyl transferase is a histone methyl transferase.

In alternative embodiments, provided are methods as provided herein, wherein the drug therapy is a receptor tyrosine kinase (RTK) inhibitor therapy, and inhibition or depletion of methyl transferase gene, transcript (message) and/or protein expression or activity sensitizes, increases sensitivity to or re-sensitizes a cancer stem cell or a tumor stem cell to a Receptor Tyrosine Kinase (RTK) inhibitor therapy.

In alternative embodiments of the methods, the drug therapy is or comprises administration of at least one growth factor inhibitor, which optionally comprises a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor;

wherein optionally the combination or the therapeutic combination comprises: (i) an inhibitor or depleter of a Src or a Tank Binding Kinase-1 (TBK1) protein or an inhibitor of Src or TBK1 protein activation, wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™, and (ii) an RTK inhibitor, wherein optionally the RTK inhibitor is a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor or a combination thereof.

In alternative embodiments of the methods:

(a) the at least one compound, composition or formulation, or combination of compounds, is formulated as a pharmaceutical composition;

(b) the method of (a), wherein the compound, composition or formulation or pharmaceutical composition is administered in vitro, ex vivo or in vivo, or is administered to an individual in need thereof.

(c) the method of (a) or (b), wherein the at least one compound, composition or formulation is a pharmaceutical composition is formulated for administration intravenously (IV), parenterally, nasally, topically, orally, or by liposome or targeted or vessel-targeted nanoparticle delivery;

(d) the method of any of (a) to (c), wherein the compound or composition comprises or is an inhibitor of transcription, translation or protein expression;

(e) the method of any of (a) to (d), wherein the compound or composition is a small molecule, a protein, an antibody, a monoclonal antibody, a nucleic acid, a lipid or a fat, a polysaccharide, an RNA or a DNA;

(f) the method of any of (a) to (e), wherein the compound or composition further comprises, or the method further comprises administration of: a VITAXIN™ (Applied Molecular Evolution, San Diego, Calif.) antibody, a humanized version of an LM609 monoclonal antibody, an LM609 monoclonal antibody, or any antibody that functionally blocks an $\alpha_v\beta_3$ integrin or any member of an $\alpha_v\beta_3$ integrin-comprising complex or an integrin $\alpha_v\beta_3$ (anb3)/RalB/NFkB signaling axis;

(g) the method of any of (a) to (e), wherein the compound or composition further comprises, or the method further comprises administration of, a Src inhibitor, a dasatinib, a saracatinib; a bosutinib; a NVP-BHG712, or any combination thereof.

(h) the method of any of (a) to (g), wherein the compound or composition further comprises, or the method further comprises administration of, a Growth Factor Inhibitor, an anti-metabolite inhibitor, a gemcitabine, GEMZAR™, a mitotic poison, a paclitaxel, a taxol, ABRAXANE™, an erlotinib, TARCEVA™, a lapatinib, TYKERB™, or an insulin growth factor inhibitor, or any combination thereof.

In alternative embodiments, provided are kits, blister packages, lidded blisters or a blister card or packet, clamshells, trays or shrink wraps, comprising:

(a) (i) at least one compound, composition or formulation used to practice a method as provided herein, and (ii); at least one Growth Factor Inhibitor, wherein optionally the Growth Factor Inhibitor is or comprises an anti-metabolite inhibitor, a gemcitabine, GEMZAR™, a mitotic poison, a paclitaxel, a taxol, ABRAXANE™, an erlotinib, TARCEVA™, a lapatinib, TYKERB™, or an insulin growth factor inhibitor, or any combination thereof; or, the Growth Factor Inhibitor decreases, slows or blocks new blood vessel growth, neovascularization or angiogenesis; or, wherein administering the Growth Factor Inhibitor treats or ameliorates conditions that are responsive to blocking or slowing cell growth, and/or the development of neovascularization or new blood vessels; or (b) the kit of (a), further comprising instructions for practicing a method as provided herein, wherein optionally the kit, blister package, lidded blister, blister card, packet, clamshell, tray or shrink wrap comprises: an erlotinib with either Lenalidomide or PS-1145, or Lenalidomide and PS-1145.

In alternative embodiments, provided are methods for determining the therapeutic value of a drug in treating a beta-3 ($\beta$3)-expressing, or integrin $\beta$3 (ITGB3)-expressing, cancer cell or tumor cell, wherein optionally the therapeutic value comprises the property or value of whether an individual or a patient would benefit from or respond to administration of the drug, or which individuals or patients would benefit from a combinatorial approach comprising administration of a combination of: at least one growth factor and at least one compound, composition or formulation used to practice a method as provided herein, the method comprising:

(a) (i) administering at least one compound, composition or formulation comprising or consisting of: an inhibitor or depleter of a methyl transferase gene, transcript (message) and/or protein expression or activity; or, a compound, composition or formulation that reduces or inhibits methyl transferase gene, transcript (message) and/or protein expression or activity, wherein optionally the methyl transferase is a histone methyl transferase;

(ii) administering the drug whose therapeutic value is to be determined, wherein optionally step (a)(i) is performed before step (a)(ii), or step (a)(ii) is performed before step (a)(i), step (a)(i) is performed with or about the same time as step (a)(ii); and (b) determining the therapeutic value of the drug in treating a beta-3 ($\beta$3)-expressing, or integrin $\beta$3 (ITGB3)-expressing, cancer cell or tumor cell.

In alternative embodiments, provided are Uses of a compound, composition or formulation in the manufacture of a medicament for:

preventing or slowing the development or generation of a beta-3 ($\beta$3)-expressing, or integrin $\beta$3 (ITGB3)-expressing, cancer cell or tumor cell, or preventing or slowing the development of an alpha-V ($\alpha$-5)/beta-3 ($\beta$3)-expressing cancer cell or tumor cell, or for preventing or slowing the phenotypic conversion of a cancer cell or tumor cell not expressing a beta-3 ($\beta$3), or integrin $\beta$3 (ITGB3), polypeptide to a cancer cell or tumor cell that expresses a beta-3 ($\beta$3), or integrin $\beta$3 (ITGB3), polypeptide, or for preventing or slowing the phenotypic conversion of a cancer cell or tumor cell not expressing an alpha-V ($\alpha$-5)/beta-3 ($\beta$3) polypeptide dimer to a cancer cell or tumor cell that expresses an alpha-V ($\alpha$-5)/beta-3 ($\beta$3) polypeptide dimer;

overcoming or diminishing or preventing a conversion of a cancer cell to a cancer stem cell, or acquiring a "stemness" phenotype; or, reversing, diminishing or preventing phenotypic conversion of a cancer cell to a cancer stem cell or a cancer cell having a "stemness" phenotype;

overcoming or diminishing or preventing a Growth Factor Inhibitor (GFI) resistance in a cell;

overcoming or diminishing or preventing tumor progression or metastasis of a cancer cell;

sensitizing, increasing sensitivity to or re-sensitizing a cancer stem cell or a tumor stem cell to a cancer therapy, or making a cancer stem cell or a tumor stem cell more sensitive to a cancer therapy (making the cancer therapy more effective),
wherein optionally the cancer therapy is a drug therapy or a radiation therapy,
and optionally the drug therapy is a receptor tyrosine kinase (RTK) inhibitor therapy (sensitizing, increasing sensitivity to or re-sensitizing a cancer stem cell or a tumor stem cell to a Receptor Tyrosine Kinase (RTK) inhibitor therapy);

sensitizing, increasing sensitivity to or re-sensitizing a dysfunctional cell, a tumor or cancer to a drug,
wherein optionally the drug is a Receptor Tyrosine Kinase (RTK) inhibitor, an EGFR1 inhibitor, an EGFR1/EGFR2 inhibitor or an IGF-1R inhibitor, or an erlotinib, a linsitinib, a lapatinib or a lenalidomide;

sensitizing, increasing sensitivity to or re-sensitizing a tumor that is resistant to a cancer or anti-tumor drug, or
reversing a tumor cell, a cancer cell, a cancer stem cell or a dysfunctional cell initiation or self-renewal capacity,
wherein optionally the cell is a tumor cell, a cancer cell, a cancer stem cell, or a dysfunctional cell,
wherein the compound, composition or formulation comprises or consists of: an inhibitor or depleter of a methyl transferase gene, transcript (message) and/or protein expression or activity; or, a compound, composition or formulation that reduces or inhibits methyl transferase gene, transcript (message) and/or protein expression or activity,
wherein optionally the methyl transferase is a histone methyl transferase.

In alternative embodiments, provided are combinations, or therapeutic combinations, for:
preventing or slowing the development or generation of a beta-3 (β3)-expressing, or integrin β3 (ITGB3)-expressing, cancer cell or tumor cell, or preventing or slowing the development of an alpha-V (α-5)/beta-3 (β3)-expressing cancer cell or tumor cell, or for preventing or slowing the phenotypic conversion of a cancer cell or tumor cell not expressing a beta-3 (β3), or integrin β3 (ITGB3), polypeptide to a cancer cell or tumor cell that expresses a beta-3 (β3), or integrin β3 (ITGB3), polypeptide, or for preventing or slowing the phenotypic conversion of a cancer cell or tumor cell not expressing an alpha-V (α-5)/beta-3 (β3) polypeptide dimer to a cancer cell or tumor cell that expresses an alpha-V (α-5)/beta-3 (β3) polypeptide dimer;
overcoming or diminishing or preventing a conversion of a cancer cell to a cancer stem cell, or acquiring a "stemness" phenotype; or, reversing, diminishing or preventing phenotypic conversion of a cancer cell to a cancer stem cell or a cancer cell having a "stemness" phenotype;
overcoming or diminishing or preventing a Growth Factor Inhibitor (GFI) resistance in a cell;
overcoming or diminishing or preventing tumor progression or metastasis of a cancer cell;
sensitizing, increasing sensitivity to or re-sensitizing a cancer stem cell or a tumor stem cell to a cancer therapy, or making a cancer stem cell or a tumor stem cell more sensitive to a cancer therapy (making the cancer therapy more effective),
wherein optionally the cancer therapy is a drug therapy or a radiation therapy,
and optionally the drug therapy is a receptor tyrosine kinase (RTK) inhibitor therapy (sensitizing, increasing sensitivity to or re-sensitizing a cancer stem cell or a tumor stem cell to a Receptor Tyrosine Kinase (RTK) inhibitor therapy);

sensitizing, increasing sensitivity to or re-sensitizing a dysfunctional cell, a tumor or cancer to a drug,
wherein optionally the drug is a Receptor Tyrosine Kinase (RTK) inhibitor, an EGFR1 inhibitor, an EGFR1/EGFR2 inhibitor or an IGF-1R inhibitor, or an erlotinib, a linsitinib, a lapatinib or a lenalidomide;

sensitizing, increasing sensitivity to or re-sensitizing a tumor that is resistant to a cancer or anti-tumor drug, or
reversing a tumor cell, a cancer cell, a cancer stem cell or a dysfunctional cell initiation or self-renewal capacity,
wherein optionally the cell is a tumor cell, a cancer cell, a cancer stem cell, or a dysfunctional cell,
wherein the combination comprises or consists of:
(a) a compound, composition or formulation comprises or consists of: an inhibitor or depleter of a methyl transferase gene, transcript (message) and/or protein expression or activity; or, a compound, composition or formulation that reduces or inhibits methyl transferase gene, transcript (message) and/or protein expression or activity,
wherein optionally the methyl transferase is a histone methyl transferase; and
(b) a growth factor inhibitor, optionally comprising a Receptor Tyrosine Kinase (RTK) inhibitor, a Src inhibitor, an anti-metabolite inhibitor, a gemcitabine, a GEMZAR™, a mitotic poison, a paclitaxel, a taxol, an ABRAXANE™, an erlotinib, a TARCEVA™, a lapatinib, a TYKERB™, a cetuxamib, an ERBITUX™, or an insulin growth factor inhibitor.

The details of one or more exemplary embodiments are set forth in the accompanying drawings and the description below. Other features, objects, and advantages of the invention will be apparent from the description and drawings, and from the claims. All publications, patents, patent applications cited herein are hereby expressly incorporated by reference for all purposes.

BRIEF DESCRIPTION OF THE DRAWINGS

The drawings set forth herein are illustrative of embodiments as provided herein and are not meant to limit the scope of the invention as encompassed by the claims.

FIG. 3A illustrates fold expression mRNA relative to serum after ITGB3 induction of control vehicle, 0.10 µM GSKJ4, and 0.25 µM GSKJ4; FIG. 3B illustrates fold expression mRNA relative to serum after Nanog induction of control vehicle, 0.10 µM GSKJ4, and 0.25 µM GSKJ4; FIG. 3C illustrates nM Erlotinib under conditions comprising serum, no serum and no serum and GSKJ4; and FIG. 3D illustrates fold expression mRNA relative to serum after ITGB3 induction with serum, no serum and no serum and GSKJ4.

FIG. 4A and FIG. 4C graphically illustrate, and FIG. 4B schematically illustrates, that integrin β3 defines a "stem"

population, FIG. 4A graphically illustrates % change in tumor volume in naïve versus Erlotinib treated over weeks as indicated in HCC827 NSCLC xenografts, EGFR E746/A750Δ; FIG. 4B schematically illustrates integrin β3 positive versus integrin β3 negative primary and secondary tumorspheres, and FIG. 4C graphically illustrates tumorspheres per 10,000 cells in primary and secondary tumorspheres of unsorted, integrin β3 positive and integrin β3 negative sorted cells.

FIG. 7A showing β3 RNA expression (fold vs normoxia) as a function of days in HC827 cells after hypoxia; FIG. 7A showing β3 RNA expression (fold vs normoxia) as a function of amount hydrogen peroxide stress (in mM) in HC827 cells; and FIG. 7C showing β3 RNA expression (fold vs normoxia) as a function of days in 0% serum in HC827 cells (after nutrient deprivation).

FIG. 8A illustrating "closed" chromatin, also called heterochromatin, and "open" chromatin, also called euchromatin states, where methylation is modified by the indicated factors.

FIG. 10A and FIG. 10B schematically and graphically illustrate that cellular stress triggers a more open chromatin on the β3 promoter: FIG. 10A schematically illustrates a chromatin immunoprecipitation, or ChiP, to analyze the β3 promoter region for histone modifications, with H3K9ac active, H3K4me3 active, and K3K27me3 inactive; and FIG. 10B graphically illustrates that serum starvation induces histone modifications on the β3 promoter, showing fold change relative to serum as a function of H3K9ac active, H3K4me3 active, and K3K27me3 inactive.

Like reference symbols in the various drawings indicate like elements.

Figure 1:
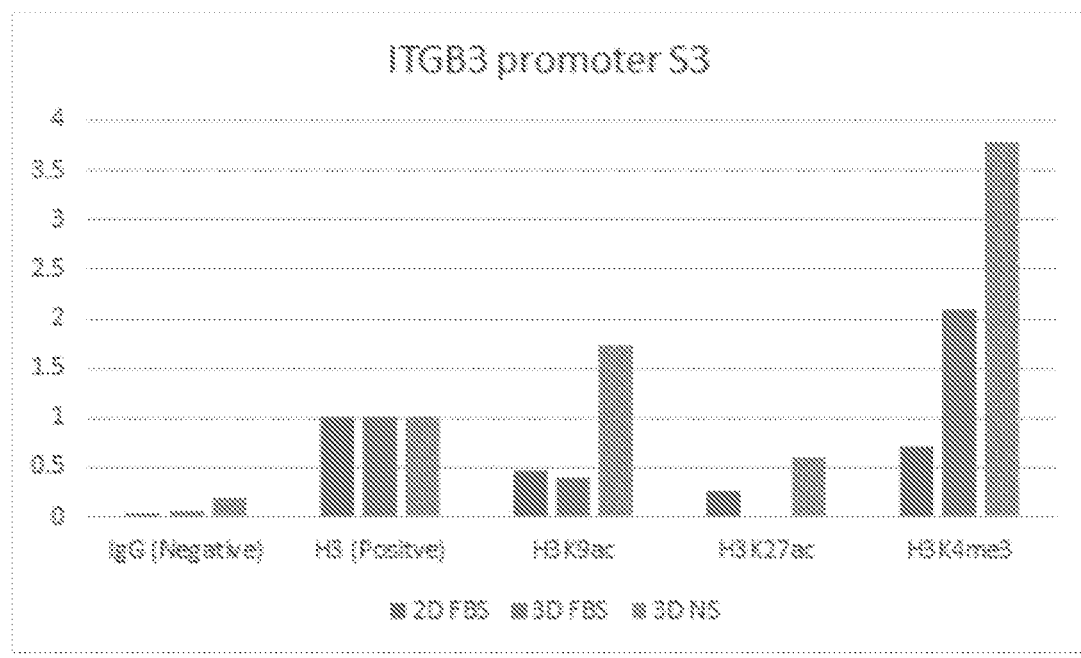
FIG. 1 graphically illustrates data showing that the induction of cancer stem cell marker ITGB3 is a result of histone acetylation and methylation at the ITGB3 promoter region that results in a more active state for gene transcription initiation. ChIPanalysis of B3-promoter region (stress/non stress) shows enrichment of H3K9ac, H3k4me3, H3K27ac are enriched in the promoter region stress induced cancer cells).

Reference will now be made in detail to various exemplary embodiments, examples of which are illustrated in the accompanying drawings. The following detailed description is provided to give the reader a better understanding of certain details of aspects and embodiments as provided herein, and should not be interpreted as a limitation on the scope of the invention.

DETAILED DESCRIPTION

In alternative embodiments, provided are compositions and methods for treating, enhancing the drug sensitivity of, and preventing the formation of cancer stems cells, including preventing or slowing the development or generation of a beta-3 (β3)-expressing, or integrin β3 (ITGB3)-expressing cancer or tumor cells. In alternative embodiments, provided for the first time is a demonstration of the function of histone acetyltransferase against drug resistant cancer stem cells. In alternative embodiments, provided for the first time is a demonstration of histone methyltransferase against drug resistant cancer stem cells. In alternative embodiments, provided are compositions and methods for sensitizing tumor stem cells to therapeutic interventions by drugs which are now considered standard of care.

In alternative embodiments, provided for the first time is a demonstration that drug treatment or cellular stress, including for example hypoxia, nutrient deprivation, oxidative stress, can lead to the expression of αVβ3 on tumor cells and the reprogramming of these cells to a stem cell fate, which is resistant to therapy.

In alternative embodiments, provided are compositions and methods for treating cancer stem cells with drugs that target methyl transferases. In alternative embodiments, compositions and methods as provided herein can be used to prevent the appearance of a beta-3 (β3) polypeptide, an integrin β3 (ITGB3) polypeptide, or an αVβ3 dimeric polypeptide on a cell, thereby: reducing the "stemness" of the cell (e.g., reducing phenotypic characteristics that contribute to "stemness"); increasing the response or sensitivity of the cell to a chemotherapeutic drug or other treatment; and/or re-sensitizing the cell a chemotherapeutic drug or other treatment. In alternative embodiments, the cell is a cancer cell.

In alternative embodiments, provided are compositions and methods for treating cancer stem cells with drugs that target acetyl transferases. In alternative embodiments, compositions and methods as provided herein can be used to prevent the appearance of a beta-3 (β3) polypeptide, an integrin β3 (ITGB3) polypeptide, or an αVβ3 dimeric polypeptide on a cell, thereby: reducing the "stemness" of the cell (e.g., reducing phenotypic characteristics that contribute to "stemness"); increasing the response or sensitivity of the cell to a chemotherapeutic drug or other treatment; and/or re-sensitizing the cell a chemotherapeutic drug or other treatment. In alternative embodiments, the cell is a cancer cell.

Provided are methods for preventing the appearance of αVβ3 through a post translational modification by administration of/using drugs that target and inhibit (partially or completely) the expression and/or activity of histone acetyl transferases. Provided are methods comprising administration of/use of drugs that specifically inhibit histone acetyl transferase enzymes, which in alternative embodiments, can prevent chromatin changes, transcriptional activation, and/or reprogramming of highly plastic cancer stem cells.

Provided are methods for preventing, or slowing the progress of (e.g., suppress), some of the epigenetic changes that contribute to cancer cell drug resistance, stemness and survival. Provided are methods comprising administration of/use of histone acetyl transferase inhibitors to suppress or inhibit tumor progression in epithelial cancer cells. Provided are methods comprising administration of/use of histone acetyl transferase inhibitors to increase tumor sensitivity to receptor tyrosine kinase inhibitors, which are considered standard of care for a variety of tumor types.

Provided for the first time is a description use of acetyltransferase inhibitors versus (vs.) drug-resistant stem cells. In alternative embodiments, acetyltransferase inhibitors are used to sensitize tumor stem cells such that the current therapies are more effective and/or can be used in decreased amounts or concentrations. In alternative embodiments, provided are compositions and methods using histone acetyl transferase inhibitors as a cancer therapy against beta-3 (β3) polypeptide-expressing or αVβ3-expressing drug resistant cancer stem cells.

Provided for the first time is a description of use of histone acetyl transferase pathway as relevant for induction of avb3 (e.g., an alpha-V (α-5)/beta-3 (β3) polypeptide dimer) expression and re-programming of cells. This is distinct from the function of tyrosine kinase inhibitors (TKIs), which have not been associated with re-programming of cells. In alternative embodiments, provided are compositions and methods that block re-programming and leave cells sensitive to (or re-sensitized to) chemotherapeutic drugs, e.g., TKIs. In alternative embodiments, provided are compositions and methods for using inhibitors of the histone acetyl transferase pathway to regulate the emergence of stem cells, e.g., emergence of stem cells from cancer cells or "normal" or progenitor cells. The inventors have found that b3 (e.g., beta-3 (β3) polypeptide, an integrin β3 (ITGB3) polypeptide) expression correlates with "stemness", as assessed in vitro and in vivo, e.g., using a xenograft mouse model. Provided herein are data demonstrating that stress induces β3 (e.g., beta-3 (β3) polypeptide, an integrin β3 (ITGB3) polypeptide) expression, which can be epigenetically regulated and/or caused by histone modifications. The inventors found that αVβ3 expression appears on tumor cells in response to drug treatment or cellular stress, including hypoxia, nutrient deprivation, oxidative stress and the like; and, that this leads to the reprogramming of these cells to a stem cell fate or "stemness" phenotype. Without benefit of alternative embodiments provided herein, these stem cells can be highly resistant to therapy, and in alternative embodiments also provided are compositions and methods to prevent, reverse, or slow the appearance of avb3 through an epigenetic mechanism using drugs that target and inhibit acetyl transferases.

In alternative embodiments also provided are compositions and methods using or comprising drugs that specifically inhibit a histone acetyl transferase enzyme, which in alternative embodiments prevents epigenetic changes and reprogramming of highly plastic cancer stem cells. In alternative embodiments also provided are compositions and methods for making epigenetic changes that contribute to cancer cell drug resistance, stemness and survival (and by practicing compositions and methods provided herein, drug resistance, stemness (e.g., the extent of the "stemness" phenotype) and (cancer cell) survival can be reduced). In alternative embodiments also provided are compositions and methods using histone acetyl transferase inhibitors to suppress tumor progression in cancer cells, e.g., an epithelial cancer cell. In alternative embodiments also provided are compositions and methods using histone acetyl transferase inhibitors to increase tumor sensitivity to anti-cancer drugs (or any chemotherapeutic agent), including for example receptor tyrosine kinase inhibitors, which are considered standard of care for a variety of tumor types.

In alternative embodiments, provided are methods using histone acetyl transferase inhibitors to determine therapeutic values in cancer cells that induce an integrin β3 (ITGB3) polypeptide expression. Embodiments described for the first time herein demonstrate a histone acetyl transferase inhibitor can be used to determine therapeutic values in cancer cells that induce ITGB3 expression.

Embodiments described for the first time herein describes use of methyltransferase inhibitors versus (vs.) drug-resistant stem cells. In alternative embodiments, methyltransferase inhibitors are used to sensitize tumor stem cells such that the current therapies are more effective and/or can be used in decreased amounts or concentrations. In alternative embodiments, provided are compositions and methods using histone methyl transferase inhibitors as a cancer therapy against beta-3 (β3) polypeptide-expressing or αVβ3-expressing drug resistant cancer stem cells.

Described herein is a limit dilution experiment demonstrating that the cancer stem cell is a tumor-initiating cell, and indicating that the β3-expressing cells contain all the "stemness" phenotype.

The inventors identified for the first time that the histone methyl transferase pathway is relevant for induction of avb3 (e.g., an alpha-V (α-5)/beta-3 (β3) polypeptide dimer) expression and re-programming of cells. This is distinct from the function of tyrosine kinase inhibitors (TKIs), which have not been associated with re-programming of cells. In alternative embodiments, provided are compositions and methods that block re-programming and leave cells sensitive to (or re-sensitized to) chemotherapeutic drugs, e.g., TKIs. In alternative embodiments, provided are compositions and methods for using inhibitors of the histone methyl transferase pathway to regulate the emergence of stem cells, e.g., emergence of stem cells from cancer cells or "normal" or progenitor cells. The inventors have found that b3 (e.g., beta-3 (β3) polypeptide, an integrin β3 (ITGB3) polypeptide) expression correlates with "stemness", as assessed in vitro and in vivo, e.g., using a xenograft mouse model. Provided here are data demonstrating that stress induces β3 (e.g., beta-3 (β3) polypeptide, an integrin β3 (ITGB3) polypeptide) expression, which can be epigenetically regulated and/or caused by histone modifications.

The inventors found that αVβ3 expression appears on tumor cells in response to drug treatment or cellular stress, including hypoxia, nutrient deprivation, oxidative stress and the like; and, that this leads to the reprogramming of these cells to a stem cell fate or "stemness" phenotype. Without benefit of this invention, these stem cells can be highly resistant to therapy, and in alternative embodiments also provided are compositions and methods to prevent, reverse, or slow the appearance of avb3 through an epigenetic mechanism using drugs that target and inhibit methyl transferases.

In alternative embodiments also provided are compositions and methods using or comprising drugs that specifically inhibit a histone methyl transferase enzyme, which in alternative embodiments prevents epigenetic changes and reprogramming of highly plastic cancer stem cells. In alternative embodiments also provided are compositions and methods for making epigenetic changes that contribute to cancer cell drug resistance, stemness and survival (and by practicing compositions and methods provided herein, drug resistance, stemness (e.g., the extent of the "stemness" phenotype) and (cancer cell) survival can be reduced). In alternative embodiments also provided are compositions and methods using histone methyl transferase inhibitors to suppress tumor progression in cancer cells, e.g., an epithelial cancer cell. In alternative embodiments also provided are compositions and methods using histone methyl transferase inhibitors to increase tumor sensitivity to anti-cancer drugs (or any chemotherapeutic agent), including for example receptor tyrosine kinase inhibitors, which are considered standard of care for a variety of tumor types.

In alternative embodiments, provided are methods using histone methyl transferase inhibitors to determine therapeutic values in cancer cells that induce an integrin β3 (ITGB3) polypeptide expression. Embodiments described for the first time herein demonstrate a histone methyl transferase inhibitor can be used to determine therapeutic values in cancer cells that induce ITGB3 expression.

Pharmaceutical Compositions

In alternative embodiments, provided are pharmaceutical compositions and methods for inhibiting an acetyl transferase gene, transcript (message) and/or protein expression. In alternative embodiments, provided are pharmaceutical compositions and methods for inhibiting a methyl transferase gene, transcript (message) and/or protein expression. In alternative embodiments, also provided are compositions and methods for inhibiting or depleting a methyl transferase gene or message (transcript), or inhibiting or abrogating expression of a methyl transferase gene or message.

In alternative embodiments, compositions provided herein, and compositions used to practice the methods provided herein, are formulated with a pharmaceutically acceptable carrier. In alternative embodiments, the pharmaceutical compositions used to practice the methods provided herein can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

Therapeutic agents as provided herein, and as used to practice the methods provided herein, can be administered alone or as a component of a pharmaceutical formulation (composition). The compounds may be formulated for administration in any convenient way for use in human or veterinary medicine. Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Formulations of the compositions provided herein and as used to practice the methods provided herein include those suitable for oral/nasal, topical, parenteral, rectal, and/or intravaginal administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect.

Pharmaceutical formulations provided herein and as used to practice the methods provided herein can be prepared according to any method known to the art for the manufacture of pharmaceuticals. Such drugs can contain sweetening agents, flavoring agents, coloring agents and preserving agents. A formulation can be admixtured with nontoxic pharmaceutically acceptable excipients which are suitable for manufacture. Formulations may comprise one or more diluents, emulsifiers, preservatives, buffers, excipients, etc. and may be provided in such forms as liquids, powders, emulsions, lyophilized powders, sprays, creams, lotions, controlled release formulations, tablets, pills, gels, on patches, in implants, etc.

Pharmaceutical formulations for oral administration can be formulated using pharmaceutically acceptable carriers well known in the art in appropriate and suitable dosages. Such carriers enable the pharmaceuticals to be formulated in unit dosage forms as tablets, geltabs, pills, powder, dragees, capsules, liquids, lozenges, gels, syrups, slurries, suspensions, etc., suitable for ingestion by the patient. Pharmaceutical preparations for oral use can be formulated as a solid excipient, optionally grinding a resulting mixture, and processing the mixture of granules, after adding suitable additional compounds, if desired, to obtain tablets or dragee cores. Suitable solid excipients are carbohydrate or protein fillers include, e.g., sugars, including lactose, sucrose, mannitol, or sorbitol; starch from corn, wheat, rice, potato, or other plants; cellulose such as methyl cellulose, hydroxypropylmethyl-cellulose, or sodium carboxy-methylcellulose; and gums including arabic and tragacanth; and proteins, e.g., gelatin and collagen. Disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations provided herein and as used to practice the methods provided herein can also be used orally using, e.g., push-fit capsules made of gelatin, as well as soft, sealed capsules made of gelatin and a coating such as glycerol or sorbitol. Push-fit capsules can contain active agents mixed with a filler or binders such as lactose or starches, lubricants such as talc or magnesium stearate, and, optionally, stabilizers. In soft capsules, the active agents can be dissolved or suspended in suitable liquids, such as fatty oils, liquid paraffin, or liquid polyethylene glycol with or without stabilizers.

Aqueous suspensions can contain an active agent (e.g., a composition provided herein or as used to practice the methods provided herein) in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil-based pharmaceuticals are particularly useful for administration hydrophobic active agents used to practice the methods provided herein. Oil-based suspensions can be formulated by suspending an active agent in a vegetable oil, such as arachis oil, olive oil, sesame oil or coconut oil, or in a mineral oil such as liquid paraffin; or a mixture of these. See e.g., U.S. Pat. No. 5,716,928 describing using essential oils or essential oil components for increasing bioavailability and reducing inter- and intra-individual variability of orally administered hydrophobic pharmaceutical compounds (see also U.S. Pat. No. 5,858,401). The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto (1997) J. Pharmacol. Exp. Ther. 281:93-102. The pharmaceutical formulations provided herein can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In practicing embodiment provided herein, the pharmaceutical compounds can also be administered by in intranasal, intraocular and intravaginal routes including suppositories, insufflation, powders and aerosol formulations (for examples of steroid inhalants, see Rohatagi (1995) J. Clin. Pharmacol. 35:1187-1193; Tjwa (1995) Ann. Allergy Asthma Immunol. 75:107-111). Suppositories formulations can be prepared by mixing the drug with a suitable non-irritating excipient which is solid at ordinary temperatures but liquid at body temperatures and will therefore melt in the body to release the drug. Such materials are cocoa butter and polyethylene glycols.

In practicing embodiments provided herein, the pharmaceutical compounds can be delivered by transdermally, by a topical route, formulated as applicator sticks, solutions, suspensions, emulsions, gels, creams, ointments, pastes, jellies, paints, powders, and aerosols.

In practicing embodiments provided herein, the pharmaceutical compounds can also be delivered as microspheres for slow release in the body. For example, microspheres can be administered via intradermal injection of drug which slowly release subcutaneously; see Rao (1995) J. Biomater Sci. Polym. Ed. 7:623-645; as biodegradable and injectable gel formulations, see, e.g., Gao (1995) Pharm. Res. 12:857-863 (1995); or, as microspheres for oral administration, see, e.g., Eyles (1997) J. Pharm. Pharmacol. 49:669-674.

In practicing embodiments provided herein, the pharmaceutical compounds can be parenterally administered, such as by intravenous (IV) administration or administration into a body cavity or lumen of an organ. These formulations can comprise a solution of active agent dissolved in a pharmaceutically acceptable carrier. Acceptable vehicles and solvents that can be employed are water and Ringer's solution, an isotonic sodium chloride. In addition, sterile fixed oils can be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated using those suitable dispersing or wetting agents and suspending agents. The sterile injectable preparation can also be a suspension in a nontoxic parenterally-acceptable diluent or solvent, such as a solution of 1,3-butanediol. The administration can be by bolus or continuous infusion (e.g., substantially uninterrupted introduction into a blood vessel for a specified period of time).

The pharmaceutical compounds and formulations provided herein and as used to practice the methods provided herein can be lyophilized. Also provided are stable lyophilized formulations comprising a composition provided herein, which can be made by lyophilizing a solution comprising a pharmaceutical provided herein on and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations provided herein and as used to practice the methods provided herein can be delivered by the use of liposomes (see also discussion, below). By using liposomes, particularly where the liposome surface carries ligands specific for target cells, or are otherwise preferentially directed to a specific organ, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587.

The formulations provided herein and as used to practice the methods provided herein can be administered for prophylactic and/or therapeutic treatments. In therapeutic applications, compositions are administered to a subject already suffering from a condition, infection or disease in an amount sufficient to cure, alleviate or partially arrest the clinical manifestations of the condition, infection or disease and its complications (a "therapeutically effective amount"). For example, in alternative embodiments, pharmaceutical compositions provided herein are administered in an amount sufficient to sensitize, increase sensitivity to or re-sensitize a tumor that is resistant to a cancer or anti-tumor drug. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

The dosage regimen also takes into consideration pharmacokinetics parameters well known in the art, i.e., the active agents' rate of absorption, bioavailability, metabolism, clearance, and the like (see, e.g., Hidalgo-Aragones (1996) J. Steroid Biochem. Mol. Biol. 58:611-617; Groning (1996) Pharmazie 51:337-341; Fotherby (1996) Contraception 54:59-69; Johnson (1995) J. Pharm. Sci. 84:1144-1146; Rohatagi (1995) Pharmazie 50:610-613; Brophy (1983) Eur. J. Clin. Pharmacol. 24:103-108; the latest Remington's, supra). The state of the art allows the clinician to determine the dosage regimen for each individual patient, active agent and disease or condition treated. Guidelines provided for similar compositions used as pharmaceuticals can be used as guidance to determine the dosage regiment, i.e., dose schedule and dosage levels, administered practicing the methods provided herein are correct and appropriate.

Single or multiple administrations of formulations can be given depending on the dosage and frequency as required and tolerated by the patient. The formulations should provide a sufficient quantity of active agent to effectively treat, prevent or ameliorate a conditions, diseases or symptoms as described herein. For example, an exemplary pharmaceutical formulation for oral administration of compositions provided herein or as used to practice the methods provided herein can be in a daily amount of between about 0.1 to 0.5 to about 20, 50, 100 or 1000 or more ug per kilogram of body weight per day. In an alternative embodiment, dosages are from about 1 mg to about 4 mg per kg of body weight per patient per day are used. Lower dosages can be used, in contrast to administration orally, into the blood stream, into a body cavity or into a lumen of an organ. Substantially higher dosages can be used in topical or oral administration or administering by powders, spray or inhalation. Actual methods for preparing parenterally or non-parenterally administrable formulations will be known or apparent to those skilled in the art and are described in more detail in such publications as Remington's, supra.

The methods provided herein can further comprise co-administration with other drugs or pharmaceuticals, e.g., compositions for treating cancer, septic shock, infection, fever, pain and related symptoms or conditions. For example, the methods and/or compositions and formulations provided herein can be co-formulated with and/or co-administered with antibiotics (e.g., antibacterial or bacteriostatic peptides or proteins), particularly those effective against gram negative bacteria, fluids, cytokines, immunoregulatory agents, anti-inflammatory agents, complement activating agents, such as peptides or proteins comprising collagen-like domains or fibrinogen-like domains (e.g., a ficolin), carbohydrate-binding domains, and the like and combinations thereof.

Nanoparticles and Liposomes

Also provided are nanoparticles and liposomal membranes comprising compounds used to practice the methods provided herein. In alternative embodiments, also provided are nanoparticles and liposomal membranes targeting tumor (cancer) stem cells and dysfunctional stem cells. In one aspect, the compositions used to practice the methods provided herein are specifically targeted to cancer cells or cancer stem cells.

In alternative embodiments, also provided are nanoparticles and liposomal membranes comprising (in addition to comprising compounds used to practice the methods provided herein) molecules, e.g., peptides or antibodies, that selectively target abnormally growing, diseased, infected, dysfunctional and/or cancer (tumor) cell receptors. In alternative embodiments, also provided are nanoparticles and liposomal membranes using IL-11 receptor and/or the GRP78 receptor to targeted receptors on cells, e.g., on tumor cells, e.g., on prostate or ovarian cancer cells. See, e.g., U.S. patent application publication no. 20060239968.

Also provided are nanocells to allow the sequential delivery of two different therapeutic agents with different modes of action or different pharmacokinetics, at least one of which comprises a composition used to practice the methods provided herein. A nanocell is formed by encapsulating a nanocore with a first agent inside a lipid vesicle containing a second agent; see, e.g., Sengupta, et al., U.S. Pat. Pub. No. 20050266067. The agent in the outer lipid compartment is released first and may exert its effect before the agent in the nanocore is released. The nanocell delivery system may be formulated in any pharmaceutical composition for delivery to patients suffering from a diseases or condition as described herein, e.g., such as a retinal age-related macular degeneration, a diabetic retinopathy, a cancer or carcinoma, a glioblastoma, a neuroma, a neuroblastoma, a colon carcinoma, a hemangioma, an infection and/or a condition with at least one inflammatory component, and/or any infectious or inflammatory disease, such as a rheumatoid arthritis, a psoriasis, a fibrosis, leprosy, multiple sclerosis, inflammatory bowel disease, or ulcerative colitis or Crohn's disease.

In one embodiment, an inhibitor or depleter of an acetyl transferase gene, transcript (message) and/or protein expression or activity is contained in the outer lipid vesicle of the nanocell, and an antiangiogenic agent provided herein is loaded into the nanocore. This arrangement allows active agents to be released first and delivered to the tumor before the tumor's blood supply is cut off by the composition provided herein.

Also provided are multilayered liposomes comprising compounds used to practice embodiments provided herein, e.g., for transdermal absorption, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, to entrap a composition provided herein.

A multilayered liposome used to practice embodiments provided herein may further include an antiseptic, an antioxidant, a stabilizer, a thickener, and the like to improve stability. Synthetic and natural antiseptics can be used, e.g., in an amount of 0.01% to 20%. Antioxidants can be used, e.g., BHT, erysorbate, tocopherol, astaxanthin, vegetable flavonoid, and derivatives thereof, or a plant-derived anti-oxidizing substance. A stabilizer can be used to stabilize liposome structure, e.g., polyols and sugars. Exemplary polyols include butylene glycol, polyethylene glycol, propylene glycol, dipropylene glycol and ethyl carbitol; examples of sugars are trehalose, sucrose, mannitol, sorbitol and chitosan, or a monosaccharides or an oligosaccharides, or a high molecular weight starch. A thickener can be used for improving the dispersion stability of constructed liposomes in water, e.g., a natural thickener or an acrylamide, or a synthetic polymeric thickener. Exemplary thickeners include natural polymers, such as acacia gum, xanthan gum, gellan gum, locust bean gum and starch, cellulose derivatives, such as hydroxy ethylcellulose, hydroxypropyl cellulose and carboxymethyl cellulose, synthetic polymers, such as polyacrylic acid, poly-acrylamide or polyvinylpyrollidone and polyvinylalcohol, and copolymers thereof or crosslinked materials.

Liposomes can be made using any method, e.g., as described in Park, et al., U.S. Pat. Pub. No. 20070042031, including method of producing a liposome by encapsulating a therapeutic product comprising providing an aqueous solution in a first reservoir; providing an organic lipid solution in a second reservoir, wherein one of the aqueous solution and the organic lipid solution includes a therapeutic product; mixing the aqueous solution with said organic lipid solution in a first mixing region to produce a liposome solution, wherein the organic lipid solution mixes with said aqueous solution so as to substantially instantaneously produce a liposome encapsulating the therapeutic product; and immediately thereafter mixing the liposome solution with a buffer solution to produce a diluted liposome solution.

Also provided are nanoparticles comprising compounds used to practice embodiments provided herein to deliver a composition provided herein as a drug-containing nanoparticles (e.g., a secondary nanoparticle), as described, e.g., in U.S. Pat. Pub. No. 20070077286. In one embodiment, also provided are nanoparticles comprising a fat-soluble drug provided herein or a fat-solubilized water-soluble drug to act with a bivalent or trivalent metal salt.

Liposomes

The compositions and formulations used to practice embodiments provided herein can be delivered by the use of liposomes. By using liposomes, particularly where the liposome surface carries ligands specific for target cells, or are otherwise preferentially directed to a specific organ or cell, e.g., cancer stem cells, one can focus the delivery of the active agent into target cells in vivo. See, e.g., U.S. Pat. Nos. 6,063,400; 6,007,839; Al-Muhammed (1996) J. Microencapsul. 13:293-306; Chonn (1995) Curr. Opin. Biotechnol. 6:698-708; Ostro (1989) Am. J. Hosp. Pharm. 46:1576-1587. For example, in one embodiment, compositions and formulations used to practice embodiments provided herein are delivered by the use of liposomes having rigid lipids having head groups and hydrophobic tails, e.g., as using a polyethyleneglycol-linked lipid having a side chain matching at least a portion the lipid, as described e.g., in US Pat App Pub No. 20080089928. In another embodiment, compositions and formulations used to practice embodiments provided herein are delivered by the use of amphoteric liposomes comprising a mixture of lipids, e.g., a mixture comprising a cationic amphiphile, an anionic amphiphile and/or neutral amphiphiles, as described e.g., in US Pat App Pub No. 20080088046, or 20080031937. In another embodiment, compositions and formulations used to practice embodiments provided herein are delivered by the use of liposomes comprising a polyalkylene glycol moiety bonded through a thioether group and an antibody also bonded through a thioether group to the liposome, as described e.g., in US Pat App Pub No. 20080014255. In another embodiment, compositions and formulations used to practice embodiments provided herein are delivered by the use of liposomes comprising glycerides, glycerophospholipids, glycerophosphinolipids, glycerophosphonolipids, sulfolipids, sphingolipids, phospholipids, isoprenolides, steroids, stearines, sterols and/or carbohydrate containing lipids, as described e.g., in US Pat App Pub No. 20070148220.

Antibodies as Pharmaceutical Compositions

In alternative embodiments, also provided are compositions and methods comprising antibodies or active fragments thereof to act as inhibitors or depleters of an acetyl transferase gene, transcript (message) and/or protein expression or activity. In alternative embodiments, provided are compositions to administer these inhibitory antibodies. In alternative embodiments, also provided are compositions and methods comprising antibodies or active fragments thereof to act as inhibitors or depleters of a methyl transferase gene, transcript (message) and/or protein expression or activity. In alternative embodiments, provided are compositions to administer these inhibitory antibodies. For example, in alternative embodiments, isolated, synthetic or recombinant antibodies that specifically bind to and inhibit acetyl transferases and/or methyl transferases are used.

In alternative aspects, an antibody for practicing embodiments provided herein can comprise a peptide or polypeptide derived from, modeled after or substantially encoded by an immunoglobulin gene or immunoglobulin genes, or fragments thereof, capable of specifically binding an antigen or epitope, see, e.g. Fundamental Immunology, Third Edition, W. E. Paul, ed., Raven Press, N.Y. (1993); Wilson (1994) J. Immunol. Methods 175:267-273; Yarmush (1992) J. Biochem. Biophys. Methods 25:85-97. In alternative aspects, an antibody for practicing embodiments provided herein includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Alternative embodiments can use "humanized" antibodies, including forms of non-human (e.g., murine) antibodies that are chimeric antibodies comprising minimal sequence (e.g., the antigen binding fragment) derived from non-human immunoglobulin. In alternative embodiments, humanized antibodies are human immunoglobulins in which residues from a hypervariable region (HVR) of a recipient (e.g., a human antibody sequence) are replaced by residues from a hypervariable region (HVR) of a non-human species (donor antibody) such as mouse, rat, rabbit or nonhuman primate having the desired specificity, affinity, and capacity. In alternative embodiments, framework region (FR) residues of the human immunoglobulin are replaced by corresponding non-human residues to improve antigen binding affinity.

In alternative embodiments, humanized antibodies may comprise residues that are not found in the recipient antibody or the donor antibody. These modifications may be made to improve antibody affinity or functional activity. In alternative embodiments, the humanized antibody can comprise substantially all of at least one, and typically two, variable domains, in which all or substantially all of the hypervariable regions correspond to those of a non-human immunoglobulin and all or substantially all of Ab framework regions are those of a human immunoglobulin sequence.

In alternative embodiments, a humanized antibody used to practice embodiments provided herein can comprise at least a portion of an immunoglobulin constant region (Fc), typically that of or derived from a human immunoglobulin.

However, in alternative embodiments, completely human antibodies also can be used to practice embodiments provided herein, including human antibodies comprising amino acid sequence which corresponds to that of an antibody produced by a human. This definition of a human antibody specifically excludes a humanized antibody comprising non-human antigen binding residues.

In alternative embodiments, antibodies used to practice embodiments provided herein comprise "affinity matured" antibodies, e.g., antibodies comprising with one or more alterations in one or more hypervariable regions which result in an improvement in the affinity of the antibody for antigen; e.g., a histone methyl and/or acetyl transferase, compared to a parent antibody which does not possess those alteration(s). In alternative embodiments, antibodies used to practice embodiments provided herein are matured antibodies having nanomolar or even picomolar affinities for the target antigen, e.g., a histone methyl and/or acetyl transferase. Affinity matured antibodies can be produced by procedures known in the art.

Antisense, siRNAs and microRNAs as Pharmaceutical Compositions

In alternative embodiments, also provided are compositions and methods for inhibiting or depleting an acetyl transferase gene or message (transcript), or inhibiting or abrogating expression of an acetyl transferase gene or message. In alternative embodiments, also provided are compositions and methods for inhibiting or depleting a methyl transferase gene or message (transcript), or inhibiting or abrogating expression of a methyl transferase gene or message. In alternative embodiments, this is achieved by administration of inhibitory nucleic acids, e.g., siRNA, antisense nucleic acids, and/or inhibitory microRNAs.

In alternative embodiments, compositions used to practice embodiments provided herein are formulated with a pharmaceutically acceptable carrier. In alternative embodiments, the pharmaceutical compositions used to practice embodiments provided herein can be administered parenterally, topically, orally or by local administration, such as by aerosol or transdermally. The pharmaceutical compositions can be formulated in any way and can be administered in a variety of unit dosage forms depending upon the condition or disease and the degree of illness, the general medical condition of each patient, the resulting preferred method of administration and the like. Details on techniques for formulation and administration are well described in the scientific and patent literature, see, e.g., the latest edition of Remington's Pharmaceutical Sciences, Maack Publishing Co, Easton Pa. ("Remington's").

While the invention is not limited by any particular mechanism of action: microRNAs (miRNAs) are short (20-24 nt) non-coding RNAs that are involved in post-transcriptional regulation of gene expression in multicellular organisms by affecting both the stability and translation of mRNAs. miRNAs are transcribed by RNA polymerase II as part of capped and polyadenylated primary transcripts (pri-miRNAs) that can be either protein-coding or non-coding. The primary transcript is cleaved by the Drosha ribonuclease III enzyme to produce an approximately 70-nt stem-loop precursor miRNA (pre-miRNA), which is further cleaved by the cytoplasmic Dicer ribonuclease to generate the mature miRNA and antisense miRNA star (miRNA*) products. The mature miRNA is incorporated into a RNA-induced silencing complex (RISC), which recognizes target mRNAs through imperfect base pairing with the miRNA and most commonly results in translational inhibition or destabilization of the target mRNA.

In alternative embodiments pharmaceutical compositions used to practice embodiments provided herein are administered in the form of a dosage unit, e.g., a tablet, capsule, bolus, spray. In alternative embodiments, pharmaceutical compositions comprise a compound, e.g., an antisense nucleic acid, e.g., an siRNA or a microRNA, in a dose: e.g., 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 270 mg, 280 mg, 285 mg, 290 mg, 295 mg, 300 mg, 305 mg, 310 mg, 315 mg, 320 mg, 325 mg, 330 mg, 335 mg, 340 mg, 345 mg, 350 mg, 355 mg, 360 mg, 365 mg, 370 mg, 375 mg, 380 mg, 385 mg, 390 mg, 395 mg, 400 mg, 405 mg, 410 mg, 415 mg, 420 mg, 425 mg, 430 mg, 435 mg, 440 mg, 445 mg, 450 mg, 455 mg, 460 mg, 465 mg, 470 mg, 475 mg, 480 mg, 485 mg, 490 mg, 495 mg, 500 mg, 505 mg, 510 mg, 515 mg, 520 mg, 525 mg, 530 mg, 535 mg, 540 mg, 545 mg, 550 mg, 555 mg, 560 mg, 565 mg, 570 mg, 575 mg, 580 mg, 585 mg, 590 mg, 595 mg, 600 mg, 605 mg, 610 mg, 615 mg, 620 mg, 625 mg, 630 mg, 635 mg, 640 mg, 645 mg, 650 mg, 655 mg, 660 mg, 665 mg, 670 mg, 675 mg, 680 mg, 685 mg, 690 mg, 695 mg, 700 mg, 705 mg, 710 mg, 715 mg, 720 mg, 725 mg, 730 mg, 735 mg, 740 mg, 745 mg, 750 mg, 755 mg, 760 mg, 765 mg, 770 mg, 775 mg, 780 mg, 785 mg, 790 mg, 795 mg, or 800 mg or more.

In alternative embodiments, an siRNA or a microRNA used to practice embodiments provided herein is administered as a pharmaceutical agent, e.g., a sterile formulation, e.g., a lyophilized siRNA or microRNA that is reconstituted with a suitable diluent, e.g., sterile water for injection or sterile saline for injection. In alternative embodiments the reconstituted product is administered as a subcutaneous injection or as an intravenous infusion after dilution into saline. In alternative embodiments the lyophilized drug product comprises siRNA or microRNA prepared in water for injection, or in saline for injection, adjusted to pH 7.0-9.0 with acid or base during preparation, and then lyophilized. In alternative embodiments a lyophilized siRNA or microRNA used in embodiments provided herein is between about 25 to 800 or more mg, or about 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of a siRNA or microRNA. The lyophilized siRNA or microRNA can be packaged in a 2 mL Type I, clear glass vial (e.g., ammonium sulfate-treated), e.g., stoppered with a bromobutyl rubber closure and sealed with an aluminum overseal.

In alternative embodiments, also provided are compositions and methods comprising in vivo delivery of antisense nucleic acids, e.g., siRNA or microRNAs. In practicing embodiments provided herein, the antisense nucleic acids, siRNAs, or microRNAs can be modified, e.g., in alternative embodiments, at least one nucleotide of antisense nucleic acid, e.g., siRNA or microRNA, construct is modified, e.g., to improve its resistance to nucleases, serum stability, target specificity, blood system circulation, tissue distribution, tissue penetration, cellular uptake, potency, and/or cell-permeability of the polynucleotide. In alternative embodiments, the antisense nucleic acid, siRNA or microRNA construct is unmodified. In other embodiments, at least one nucleotide in the antisense nucleic acid, siRNA or microRNA construct is modified.

In alternative embodiments, guide strand modifications are made to increase nuclease stability, and/or lower interferon induction, without significantly decreasing antisense nucleic acid, siRNA or microRNA activity (or no decrease in antisense nucleic acid, siRNA or microRNA activity at all). In certain embodiments, the modified antisense nucleic acid, siRNA or microRNA constructs have improved stability in serum and/or cerebral spinal fluid compared to an unmodified structure having the same sequence.

In alternative embodiments, a modification includes a 2'-H or 2'-modified ribose sugar at the second nucleotide from the 5'-end of the guide sequence. In alternative embodiments, the guide strand (e.g., at least one of the two single-stranded polynucleotides) comprises a 2'-O-alkyl or 2'-halo group, such as a 2'-O-methyl modified nucleotide, at the second nucleotide on the 5'-end of the guide strand, or, no other modified nucleotides. In alternative embodiments, polynucleotide constructs having such modification may have enhanced target specificity or reduced off-target silencing compared to a similar construct without the 2'-O-methyl modification at the position.

In alternative embodiments, a second nucleotide is a second nucleotide from the 5'-end of the single-stranded polynucleotide. In alternative embodiments, a "2'-modified ribose sugar" comprises ribose sugars that do not have a 2'—OH group. In alternative embodiments, a "2'-modified ribose sugar" does not include 2'-deoxyribose (found in unmodified canonical DNA nucleotides), although one or more DNA nucleotides may be included in the subject constructs (e.g., a single deoxyribonucleotide, or more than one deoxyribonucleotide in a stretch or scattered in several parts of the subject constructs). For example, the 2'-modified ribose sugar may be 2'-O-alkyl nucleotides, 2'-deoxy-2'-fluoro nucleotides, 2'-deoxy nucleotides, or combination thereof.

In alternative embodiments, an antisense nucleic acid, siRNA or microRNA construct used to practice embodiments provided herein comprises one or more 5'-end modifications, e.g., as described above, and can exhibit a significantly (e.g., at least about 25%, 30%, 35%, 40%, 45%, 50%, 55%, 60%, 65%, 70%, 75%, 80%, 85%, 90% or more) less "off-target" gene silencing when compared to similar constructs without the specified 5'-end modification, thus greatly improving the overall specificity of the antisense nucleic acid, siRNA or microRNA construct.

In alternative embodiments, an antisense nucleic acid, siRNA or microRNA construct to practice embodiments provided herein comprises a guide strand modification that further increase stability to nucleases, and/or lowers interferon induction, without significantly decreasing activity (or no decrease in microRNA activity at all). In alternative embodiments, the 5'-stem sequence comprises a 2'-modified ribose sugar, such as 2'-O-methyl modified nucleotide, at the second nucleotide on the 5'-end of the polynucleotide, or, no other modified nucleotides. In alternative embodiments the hairpin structure having such modification has enhanced target specificity or reduced off-target silencing compared to a similar construct without the 2'-O-methyl modification at same position.

In alternative embodiments, the 2'-modified nucleotides are some or all of the pyrimidine nucleotides (e.g., C/U). Examples of 2'-O-alkyl nucleotides include a 2'-O-methyl nucleotide, or a 2'-O-allyl nucleotide. In alternative embodiments, the modification comprises a 2'-O-methyl modification at alternative nucleotides, starting from either the first or the second nucleotide from the 5'-end. In alternative embodiments, the modification comprises a 2'-O-methyl modification of one or more randomly selected pyrimidine nucleotides (C or U). In alternative embodiments, the modification comprises a 2'-O-methyl modification of one or more nucleotides within the loop.

In alternative embodiments, the modified nucleotides are modified on the sugar moiety, the base, and/or the phosphodiester linkage. In alternative embodiments the modification comprise a phosphate analog, or a phosphorothioate linkage; and the phosphorothioate linkage can be limited to one or more nucleotides within the loop, a 5'-overhang, and/or a 3'-overhang.

In alternative embodiments, the phosphorothioate linkage may be limited to one or more nucleotides within the loop, and 1, 2, 3, 4, 5, or 6 more nucleotide(s) of the guide sequence within the double-stranded stem region just 5' to the loop. In alternative embodiments, the total number of nucleotides having the phosphorothioate linkage may be about 12-14. In alternative embodiments, all nucleotides having the phosphorothioate linkage are not contiguous. In alternative embodiments, the modification comprises a 2'-O-methyl modification, or, no more than 4 consecutive nucleotides are modified. In alternative embodiments, all nucleotides in the 3'-end stem region are modified. In alternative embodiments, all nucleotides 3' to the loop are modified.

In alternative embodiments, the 5'- or 3'-stem sequence comprises one or more universal base-pairing nucleotides. In alternative embodiments universal base-pairing nucleotides include extendable nucleotides that can be incorporated into a polynucleotide strand (either by chemical synthesis or by a polymerase), and pair with more than one pairing type of specific canonical nucleotide. In alternative embodiments, the universal nucleotides pair with any specific nucleotide. In alternative embodiments, the universal nucleotides pair with four pairings types of specific nucleotides or analogs thereof. In alternative embodiments, the universal nucleotides pair with three pairings types of specific nucleotides or analogs thereof. In alternative embodiments, the universal nucleotides pair with two pairings types of specific nucleotides or analogs thereof.

In alternative embodiments, an antisense nucleic acid, siRNA or microRNA used to practice embodiments provided herein comprises a modified nucleoside, e.g., a sugar-modified nucleoside. In alternative embodiments, the sugar-modified nucleosides can further comprise a natural or modified heterocyclic base moiety and/or a natural or modified internucleoside linkage; or can comprise modifications independent from the sugar modification. In alternative embodiments, a sugar modified nucleoside is a 2'-modified nucleoside, wherein the sugar ring is modified at the 2' carbon from natural ribose or 2'-deoxy-ribose.

In alternative embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In alternative embodiments, the bicyclic sugar moiety is an L sugar in the beta configuration.

In alternative embodiments, the bicyclic sugar moiety comprises a bridge group between the 2' and the 4'-carbon atoms. In alternative embodiments, the bridge group comprises from 1 to 8 linked biradical groups. In alternative embodiments, the bicyclic sugar moiety comprises from 1 to 4 linked biradical groups. In alternative embodiments, the bicyclic sugar moiety comprises 2 or 3 linked biradical groups.

In alternative embodiments, the bicyclic sugar moiety comprises 2 linked biradical groups. In alternative embodiments, a linked biradical group is selected from —O—, —N(R1)-, —C(R1)(R2)-, —C(R1)=C(R1)-, —C(R1)=N—, —C(=NR1)-, —Si(R1)(R2)-, —S(=O)$_2$—, —S(=O)—, —C(=O)— and —C(=S)—; where each R1 and R$_2$ is, independently, H, hydroxyl, C1 to C$_{12}$ alkyl, substituted C1-C12 alkyl, C$_2$-C12 alkenyl, substituted C$_2$-C$_{12}$ alkenyl, C$_2$-C$_{12}$ alkynyl, substituted C$_2$-C12 alkynyl, C$_2$-C20 aryl, substituted C$_2$-C20 aryl, a heterocycle radical, a substituted heterocycle radical, heteroaryl, substituted heteroaryl, C$_2$-C$_7$ alicyclic radical, substituted C$_2$-C$_7$ alicyclic radical, halogen, substituted oxy (—O—), amino, substituted amino, azido, carboxyl, substituted carboxyl, acyl, substituted acyl, CN, thiol, substituted thiol, sulfonyl (S(=O)$_2$—H), substituted sulfonyl, sulfoxyl (S(=O)—H) or substituted sulfoxyl; and each substituent group is, independently, halogen, C1-C$_{12}$ alkyl, substituted C1-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, amino, substituted amino, acyl, substituted acyl, C1-C$_{12}$ aminoalkyl, C1-C$_{12}$ aminoalkoxy, substituted C1-C$_{12}$ aminoalkyl, substituted C1-C$_{12}$ aminoalkoxy or a protecting group.

In alternative embodiments, the bicyclic sugar moiety is bridged between the 2' and 4' carbon atoms with a biradical group selected from —O—(CH$_2$)x-, —O—CH$_2$—, —O—CH$_2$CH$_2$—, —O—CH(alkyl)-, —NH—(CH2)P—, —N(alkyl)-(CH$_2$)x-, —O—CH(alkyl)-, —(CH(alkyl))-(CH2)x-, —NH—O—(CH2)x-, —N(alkyl)-O—(CH2)x-, or —O—N(alkyl)-(CH$_2$)x-, wherein x is 1, 2, 3, 4 or 5 and each alkyl group can be further substituted. In certain embodiments, x is 1, 2 or 3.

In alternative embodiments, a 2'-modified nucleoside comprises a 2'-substituent group selected from halo, allyl, amino, azido, SH, CN, OCN, CF$_3$, OCF$_3$, O—, S—, or N(Rm)-alkyl; O—, S—, or N(Rm)-alkenyl; O—, S— or N(Rm)-alkynyl; O-alkylenyl-O-alkyl, alkynyl, alkaryl, aralkyl, O-alkaryl, O-aralkyl, O(CH$_2$)$_2$SCH$_3$, O—(CH$_2$)$_2$—O—N(Rm)(Rn) or O—CH2-C(=O)—N(Rm)(Rn), where each Rm and Rn is, independently, H, an amino protecting group or substituted or unsubstituted C1-C10 alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In alternative embodiments, a 2'-modified nucleoside comprises a 2'-substituent group selected from F, O—CH$_3$, and OCH$_2$CH2OCH$_3$.

In alternative embodiments, a sugar-modified nucleoside is a 4'-thio modified nucleoside. In alternative embodiments, a sugar-modified nucleoside is a 4'-thio-2'-modified nucleoside. In alternative embodiments a 4'-thio modified nucleoside has a .beta.-D-ribonucleoside where the 4'-O replaced with 4'-S. A 4'-thio-2'-modified nucleoside is a 4'-thio modified nucleoside having the 2'-OH replaced with a 2'-substituent group. In alternative embodiments 2'-substituent groups include 2'-OCH$_3$, 2'—O—(CH2)$_2$—OCH$_3$, and 2'-F.

In alternative embodiments, a modified oligonucleotide used to practice embodiments provided herein comprises one or more internucleoside modifications. In alternative embodiments, each internucleoside linkage of a modified oligonucleotide is a modified internucleoside linkage. In alternative embodiments, a modified internucleoside linkage comprises a phosphorus atom.

In alternative embodiments, a modified antisense nucleic acid, siRNA or microRNA comprises at least one phosphorothioate internucleoside linkage. In certain embodiments, each internucleoside linkage of a modified oligonucleotide is a phosphorothioate internucleoside linkage.

In alternative embodiments, a modified internucleoside linkage does not comprise a phosphorus atom. In alternative embodiments, an internucleoside linkage is formed by a short chain alkyl internucleoside linkage. In alternative embodiments, an internucleoside linkage is formed by a cycloalkyl internucleoside linkages. In alternative embodiments, an internucleoside linkage is formed by a mixed heteroatom and alkyl internucleoside linkage. In alternative embodiments, an internucleoside linkage is formed by a mixed heteroatom and cycloalkyl internucleoside linkages. In alternative embodiments, an internucleoside linkage is formed by one or more short chain heteroatomic internucleoside linkages. In alternative embodiments, an internucleoside linkage is formed by one or more heterocyclic internucleoside linkages. In alternative embodiments, an internucleoside linkage has an amide backbone, or an internucleoside linkage has mixed N, O, S and CH2 component parts.

In alternative embodiments, a modified oligonucleotide comprises one or more modified nucleobases. In certain embodiments, a modified oligonucleotide comprises one or more 5-methylcytosines, or each cytosine of a modified oligonucleotide comprises a 5-methylcytosine.

In alternative embodiments, a modified nucleobase comprises a 5-hydroxymethyl cytosine, 7-deazaguanine or 7-deazaadenine, or a modified nucleobase comprises a 7-deaza-adenine, 7-deazaguanosine, 2-aminopyridine or a 2-pyridone, or a modified nucleobase comprises a 5-substituted pyrimidines, 6-azapyrimidines and N-2, N-6 and O-6 substituted purines, or a 2 aminopropyladenine, 5-propynyluracil or a 5-propynylcytosine.

In alternative embodiments, a modified nucleobase comprises a polycyclic heterocycle, or a tricyclic heterocycle; or, a modified nucleobase comprises a phenoxazine derivative, or a phenoxazine further modified to form a nucleobase or G-clamp.

Therapeutically Effective Amount and Doses

In alternative embodiments, compounds, compositions, pharmaceutical compositions and formulations used to practice embodiments provided herein can be administered for prophylactic and/or therapeutic treatments; for example, also provided are compositions and methods for increasing the growth-inhibiting effectiveness of an anti-cancer drug, e.g., a Growth Factor inhibitor on a cell, e.g., a cancer cell, or, a method for re-sensitizing a cell to a Growth Factor Inhibitor. In alternative embodiments, also provided are compositions and methods for treating, preventing or ameliorating: a disease or condition associated with dysfunctional stem cells or cancer stem cells (a "therapeutically effective amount"). In the methods provided herein, a pharmaceutical composition is administered in an amount sufficient to treat (e.g., ameliorate) or prevent a disease or condition associated with dysfunctional stem cells or cancer stem cells. The amount of pharmaceutical composition adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age and the like. In calculating the dosage regimen for a patient, the mode of administration also is taken into consideration.

Kits and Instructions

Also provided are kits comprising compositions for practicing the methods and uses as provided herein, including instructions for use thereof. In alternative embodiments, also provided are kits, blister packages, lidded blisters or blister cards or packets, clamshells, trays or shrink wraps comprising a combination of compounds.

In alternative embodiments, the combination of compounds comprises: acetyl transferase inhibitors and, e.g.:
(1) at least one compound comprising or consisting of:
(i) an inhibitor or depleter of integrin $\alpha_v\beta_3$ (anb3), or an inhibitor of integrin $\alpha_v\beta_3$ (anb3) protein activity, or an inhibitor of the formation or activity of an integrin anb3/RalB signaling complex, or an inhibitor of the formation or signaling activity of an integrin $\alpha_v\beta_3$ (anb3)/RalB/NFkB signaling axis,
wherein optionally the inhibitor of integrin $\alpha_v\beta_3$ protein activity is an allosteric inhibitor of integrin $\alpha_v\beta_3$ protein activity;
(ii) an inhibitor or depleter of RalB protein or an inhibitor of RalB protein activation,
wherein optionally the inhibitor of RalB protein activity is an allosteric inhibitor of RalB protein activity;
(iii) an inhibitor or depleter of Src or a Tank Binding Kinase (TBK1) protein or an inhibitor of Src or TBK1 protein activation,
wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™,
and optionally the inhibitor of the Src or the TBK1 protein activity is an allosteric inhibitor of Src or TBK1 protein activity;
(iv) an inhibitor or depleter of NFKB or IRF3 protein or an inhibitor of RalB protein activation,
wherein optionally the inhibitor of NFKB or IRF3 protein activity is an allosteric inhibitor of NFKB or IRF3 protein activity; or
(v) any combination of (i) to (iv); and/or
(2) at least one Growth Factor Inhibitor.

In alternative embodiments, the combination of compounds comprises: methyl transferase inhibitors and, e.g.:
(1) at least one compound comprising or consisting of:
(i) an inhibitor or depleter of integrin $\alpha_v\beta_3$ (anb3), or an inhibitor of integrin $\alpha_v\beta_3$ (anb3) protein activity, or an inhibitor of the formation or activity of an integrin anb3/RalB signaling complex, or an inhibitor of the formation or signaling activity of an integrin $\alpha_v\beta_3$ (anb3)/RalB/NFkB signaling axis,
wherein optionally the inhibitor of integrin $\alpha_v\beta_3$ protein activity is an allosteric inhibitor of integrin $\alpha_v\beta_3$ protein activity;
(ii) an inhibitor or depleter of RalB protein or an inhibitor of RalB protein activation,
wherein optionally the inhibitor of RalB protein activity is an allosteric inhibitor of RalB protein activity;
(iii) an inhibitor or depleter of Src or a Tank Binding Kinase (TBK1) protein or an inhibitor of Src or TBK1 protein activation,
wherein optionally the inhibitor of the Src or the TBK1 protein activity is an amlexanox (or 2-amino-7-isopropyl-5-oxo-5H-chromeno[2,3-b]pyridine-3-carboxylic acid) or APHTHASOL™,
and optionally the inhibitor of the Src or the TBK1 protein activity is an allosteric inhibitor of Src or TBK1 protein activity;
(iv) an inhibitor or depleter of NFKB or IRF3 protein or an inhibitor of RalB protein activation,
wherein optionally the inhibitor of NFKB or IRF3 protein activity is an allosteric inhibitor of NFKB or IRF3 protein activity; or
(v) any combination of (i) to (iv); and/or
(2) at least one Growth Factor Inhibitor.

In alternative embodiments, the kit further comprises instructions for practicing a method as provided herein.

The invention will be further described with reference to the following examples; however, it is to be understood that the exemplary embodiments provided herein are or the invention are not limited to such examples.

EXAMPLES

Example 1: Methods Provided Herein are Effective for Sensitizing and Re-Sensitizing Cancer Cells to Anticancer Drug Treatments and Growth Factor Inhibitors The data presented herein, for example, as illustrated in the Figures, demonstrates the effectiveness of the compositions and methods as provided herein in sensitizing and re-sensitizing cancer stem cells to anti-cancer drugs, including growth factor inhibitors, and validates this invention's therapeutic approach to overcome drug insensitivity in stem cells.

FIG. 1 graphically illustrates data showing that the induction of cancer stem cell marker ITGB3 is a result of histone acetylation and methylation at the ITGB3 promoter region that results in a more active state for gene transcription initiation. ChIPanalysis of B3-promoter region (stress/non stress) shows enrichment of H3K9ac, H3k4me3, H3K27ac are enriched in the promoter region stress induced cancer cells).

Figure 2:
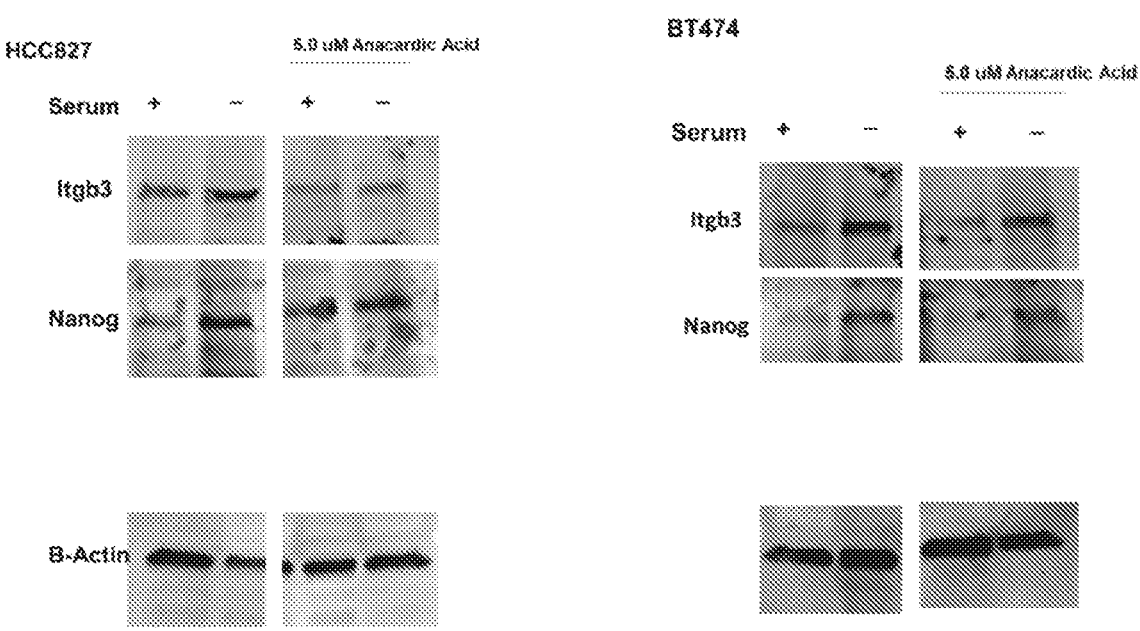
FIG. 2 graphically illustrates data showing that ITGB3 induction is suppressed in the presence of histone acetyl-transferase (HAT) inhibitor anacardic acid.

FIG. 2 graphically illustrates data showing that ITGB3 induction is suppressed in the presence of histone acetyltransferase (HAT) inhibitor anacardic acid.

Figure 3A:
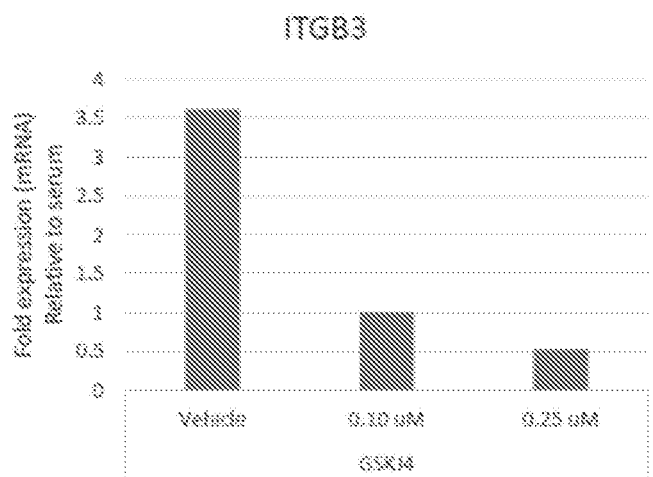
FIG. 3A, FIG. 3B, FIG. 3C and FIG. 3D graphically illustrate data showing that treatment with histone modification inhibitor(s) suppresses the stress induced drug resistant phenotype.
Figure 3B:
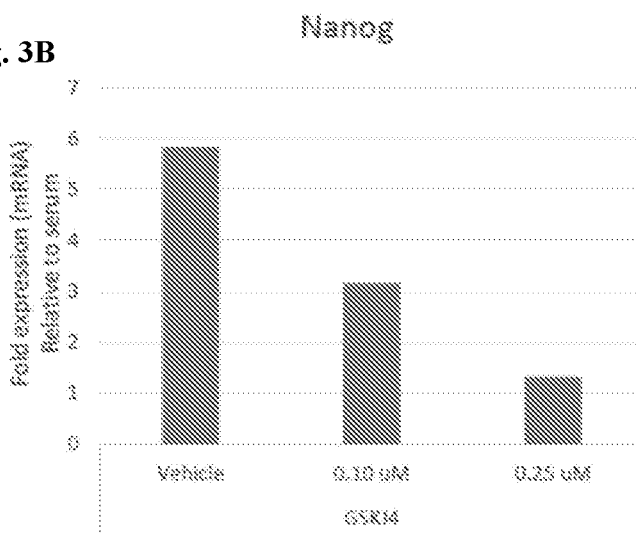
Figure 3C:
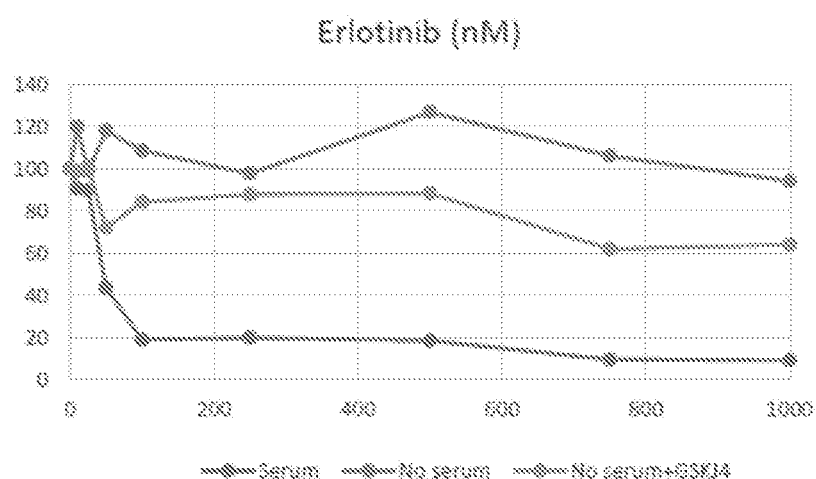
Figure 3D:
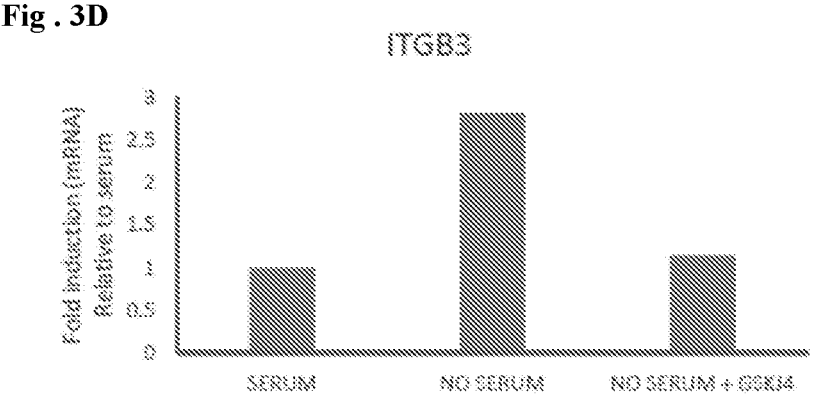
Figures 5A, 5B, 5C:
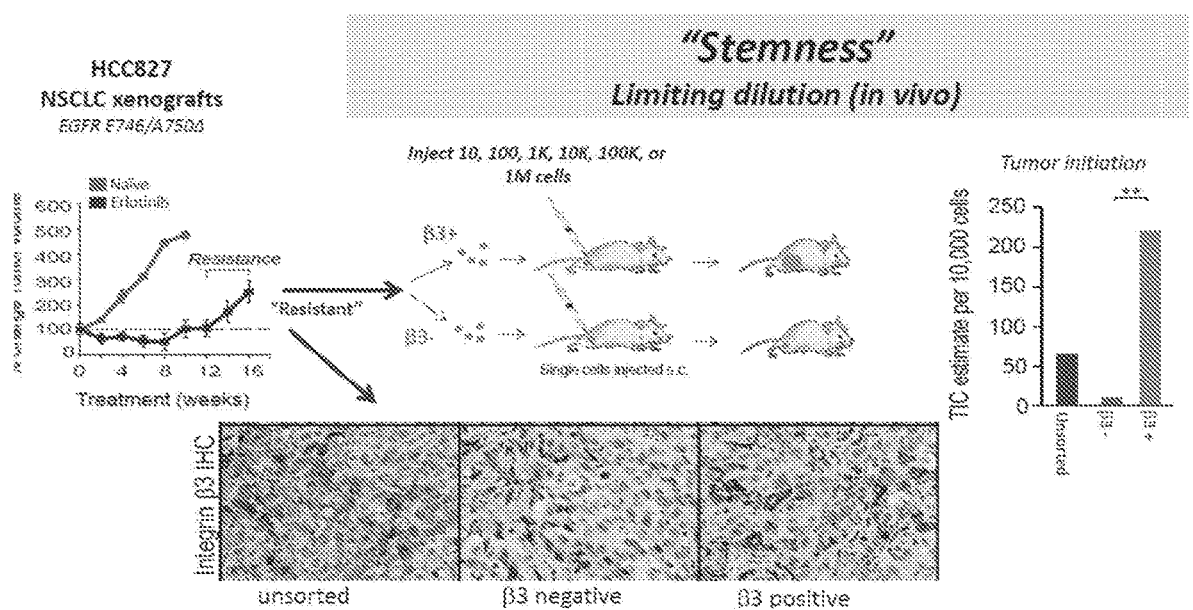
FIG. 5A and FIG. 5C graphically illustrate, and FIG. 5B schematically illustrates, that integrin β3 defines a "stem" population, FIG. 5A graphically illustrates % change in tumor volume in naïve versus Erlotinib treated over weeks as indicated in HCC827 NSCLC xenografts, EGFR E746/A750Δ.
FIG. 5B illustrates images of integrin β3 stained cells in unsorted, β3 negative sorted and β3 positive cells sorted, and FIG. 5C graphically illustrates TIC estimate per 10,000 cells in unsorted, β3 negative sorted and β3 positive cells.
Figures 6A, 6B, 6C:
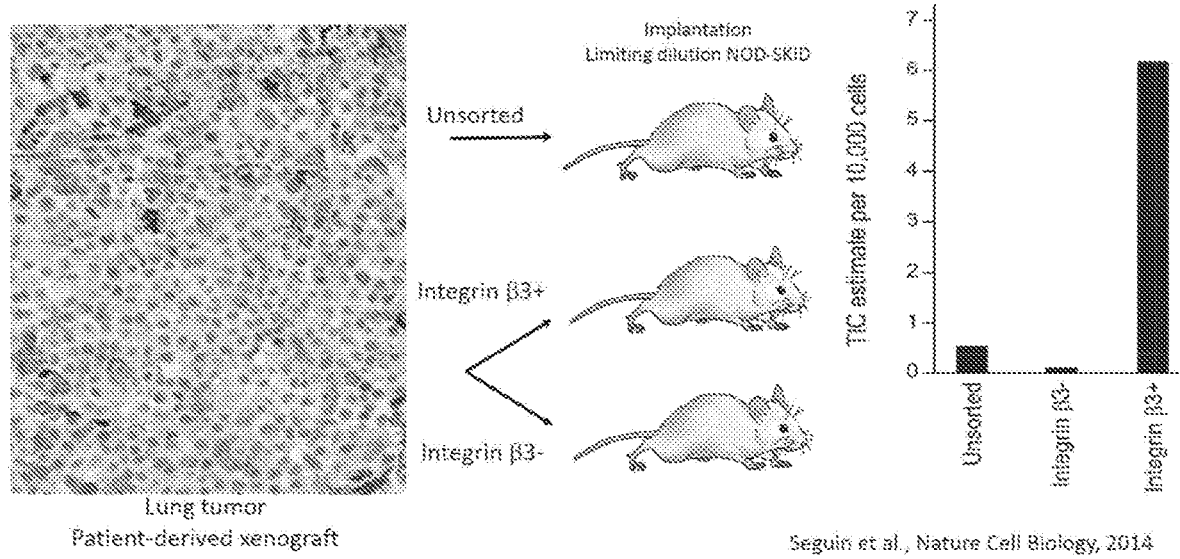
FIG. 6C graphically illustrates, and FIG. 6A and FIG. 6B schematically illustrate, that integrin β3 positive tumor cells isolated from patient-derived xenografts show enhanced tumor initiation.
FIG. 6A illustrates an image of lung tumor patient derived xenograft cells, which are then unsorted, β3 negative sorted and β3 positive cells sorted followed by implantation in NOD-SKID, and FIG. 6C graphically illustrates TIC estimate per 10,000 cells in the unsorted, β3 negative sorted and β3 positive cell populations.
Figure 7A:
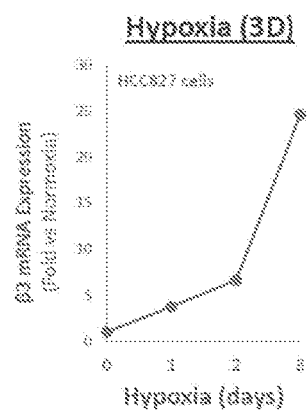
FIG. 7A, FIG. 7B and FIG. 7C graphically illustrate that multiple stresses induce β3 RNA.
Figure 7B:
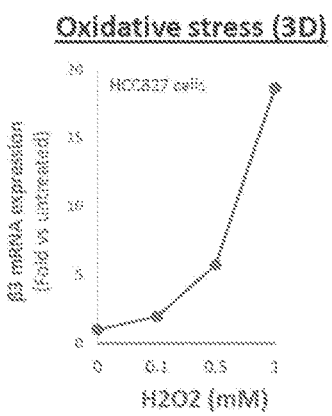
Figure 7C:
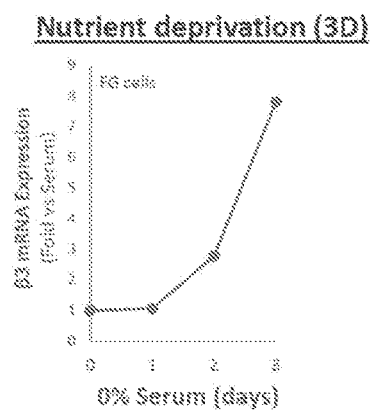
Figure 8A:
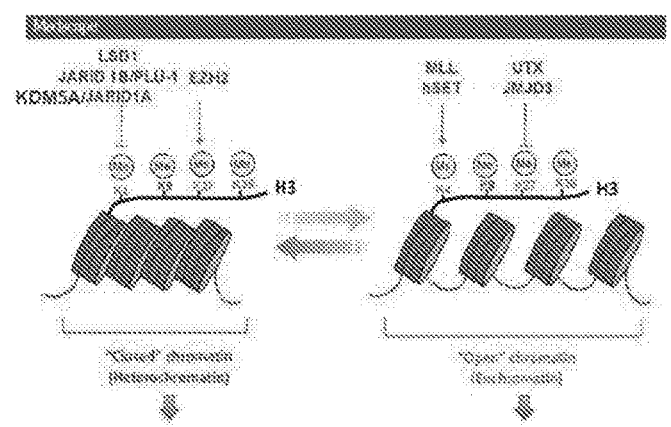
FIG. 8A schematically illustrates and FIG. 8B graphically illustrates the finding that stress-induced β3 expression correlates with increased levels of histone demethylase JMJD3, which in turn modifies H3K27me3.
Figure 8B:
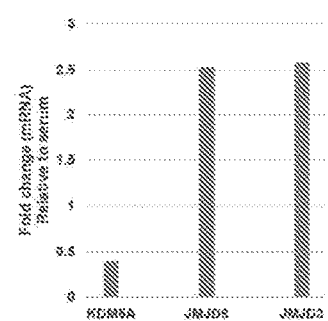
FIG. 8B graphically illustrating fold change (mRNA) relative to serum in KDM5A, JMJD6 and JMJD3 expressing cells.
Figure 9A:
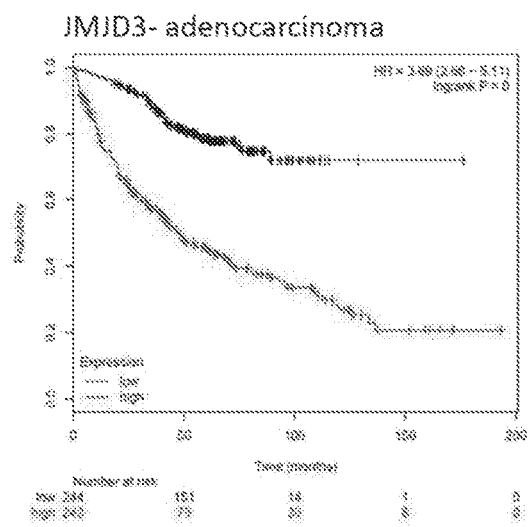
FIG. 9A and FIG. 9B graphically illustrate Kaplan Meer survival plots of JMJD3 expressing adenocarcinoma cells and JMJD3 expressing squamous cells, which illustrate that in lung adenocarcinoma cells patients with high expression of JMJD3 show significant decrease in overall survival; see Gyorffy (2013) PLos One December 18, vol 8(12)e82241.
Figure 9B:
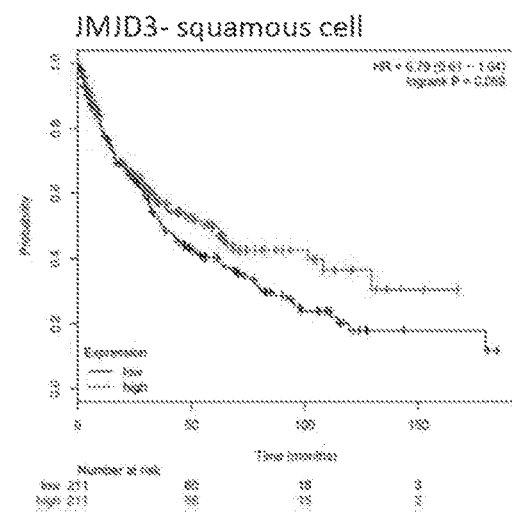
Figure 11A:
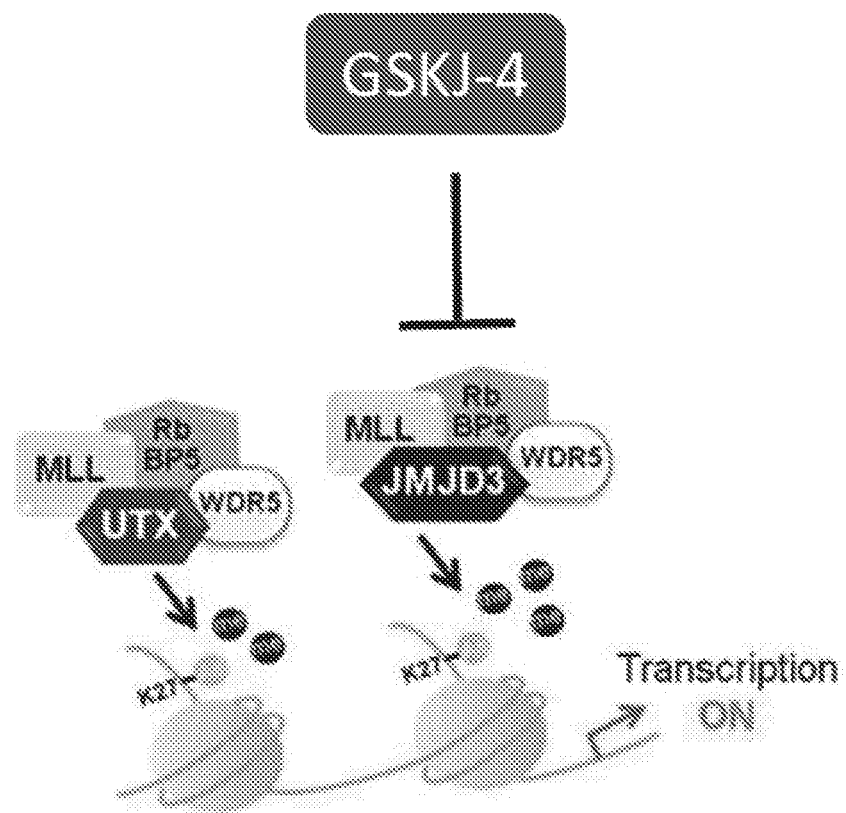
FIG. 11A schematically illustrates, and FIG. 11B, FIG. 11C, FIG. 11D and FIG. 11E graphically illustrate that GSKJ-4, which targets histone demethylase JMJD3, suppresses β3 expression as well as pluripotent genes Nanog and OCT4, with the conclusion that GSKJ-4 suppresses ITGB3, Nanog and OCT4 induction by inhibiting JMJD3-targeted H3K27me3 demethylation.
Figure 11B:
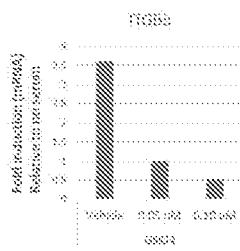
FIG. 11B, FIG. 11C, FIG. 11D and FIG. 11E graphically illustrate fold induction mRNA relative to no serum as a function of GSKJ-4 suppression of ITGB3, Nanog and OCT4 induction, with FIG. 11B, FIG. 11C, FIG. 11D and FIG. 11E illustrating levels of ITGB3, Nanog, OCT4 and SOX2, respectively.
Figure 11C:
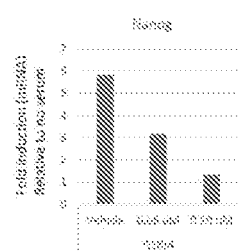
Figure 11D:
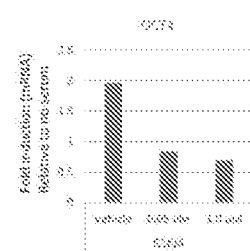
Figure 11E:
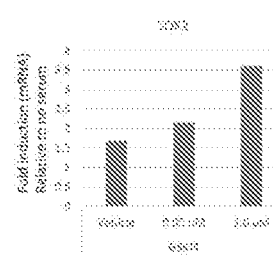

FIG. 3A, FIG. 3B, FIG. 3C and FIG. 3D graphically illustrate data showing that treatment with histone modification inhibitor(s) suppresses the stress induced drug resistant phenotype: FIG. 3A illustrates fold expression mRNA relative to serum after ITGB3 induction of control vehicle, 0.10 µM GSKJ4, and 0.25 µM GSKJ4; FIG. 3B illustrates fold expression mRNA relative to serum after Nanog induction of control vehicle, 0.10 µM GSKJ4, and 0.25 µM GSKJ4; FIG. 3C illustrates nM Erlotinib under conditions comprising serum, no serum and no serum and GSKJ4; and FIG. 3D illustrates fold expression mRNA relative to serum after ITGB3 induction with serum, no serum and no serum and GSKJ4.

Figure 12A:
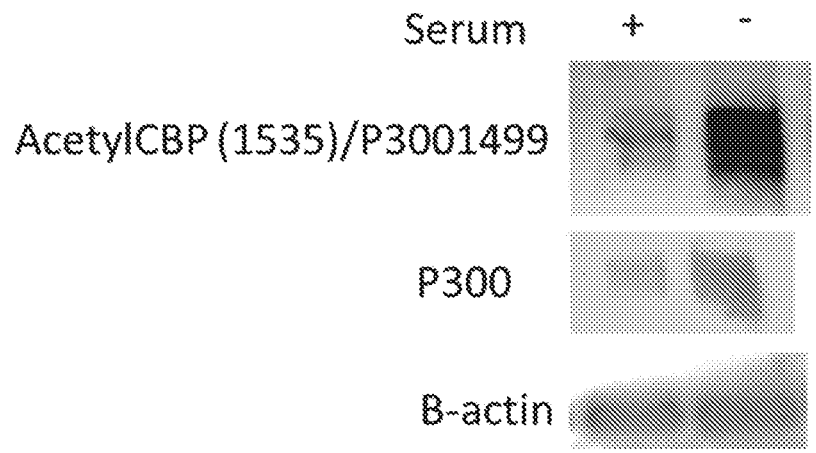
FIG. 12A and FIG. 12B illustrate images of gels showing that inhibition of histone acetyl transferase activity (HAT) by a pharmacological (anacardic acid) or a genetic approach prevents stress induced integrin β3 expression and downstream stem cell genes, as discussed in detail in Example 1, below.
Figure 12B:
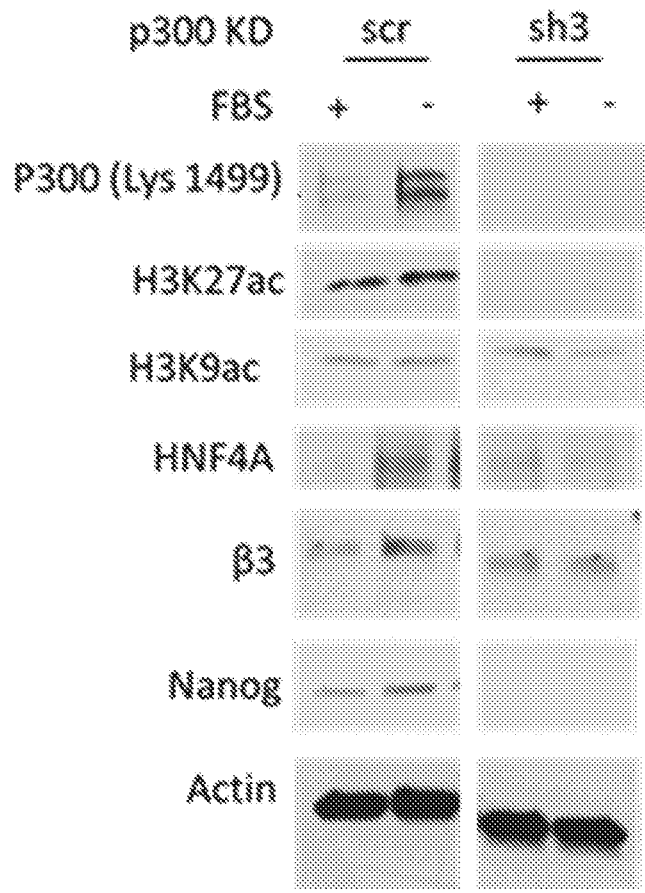

FIGS. 12A and 12B illustrate data showing the knockdown of P300 histone acetyl transferase (HAT), a known enzyme that targets H3K27ac, in HCC827 lung cancer cells. Histone acetyl transferase (acetyl p300) activity is increased during nutrient deprivation (without serum) leading to integrin β3 expression, which prevents stress-induced expression of integrin β3 and stem cell genes. Increase in histone acetyltransferase (HAT) p300 activity leads to upregulation of integrin β3. Loss of p300 histone acetyltransferase activity prevents the upregulation of integrin β3. Similar to chemical inhibition of HAT activity with anacardic acid at 0.1 uM concentration, a genetic approach was used to knockdown p300 histone acetyl transferase (HAT), a known enzyme that targets H3K27ac prevents expression of integrin β3 and stem cell genes.

Figures 13A, 13B:
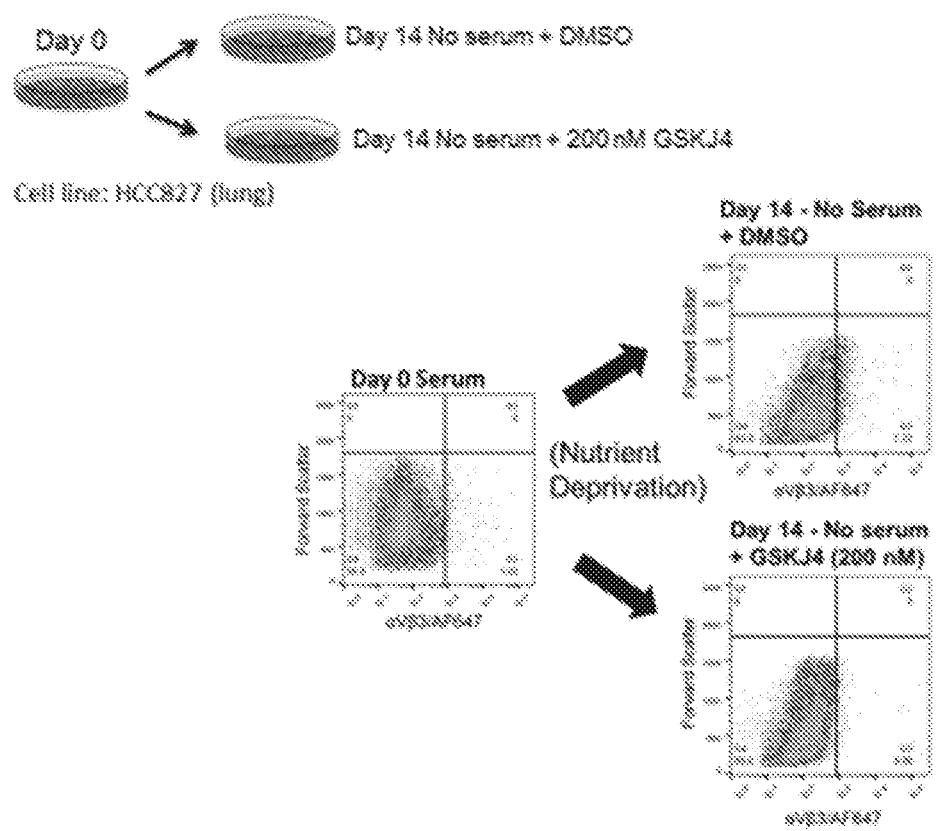
FIG. 13A illustrates the experimental protocol.
FIG. 13B illustrates images of cell sorting data showing that Histone demethylase (GSKJ4) prevents the expansion of an integrin β3 expressing stem population during nutrient deprivation (no serum), as discussed in detail in Example 1, below.

FIG. 13A illustrates the experimental protocol, a 14 day assay for cell surface induction of integrin β3 by nutrient deprivation, and FIG. 13B illustrates images of cell sorting data showing that Hi stone demethylase (GSKJ4) prevents the expansion of an integrin β3 expressing stem population during nutrient deprivation (no serum). The data shows that lung cancer cells (HCC827) treated with JMJD3 histone demethylase inhibitor GSKJ4 prevents the induction of integrin β3 gene expression and formation of the heterodimeric αVβ3 cell surface expression.

Figures 14A, 14B:
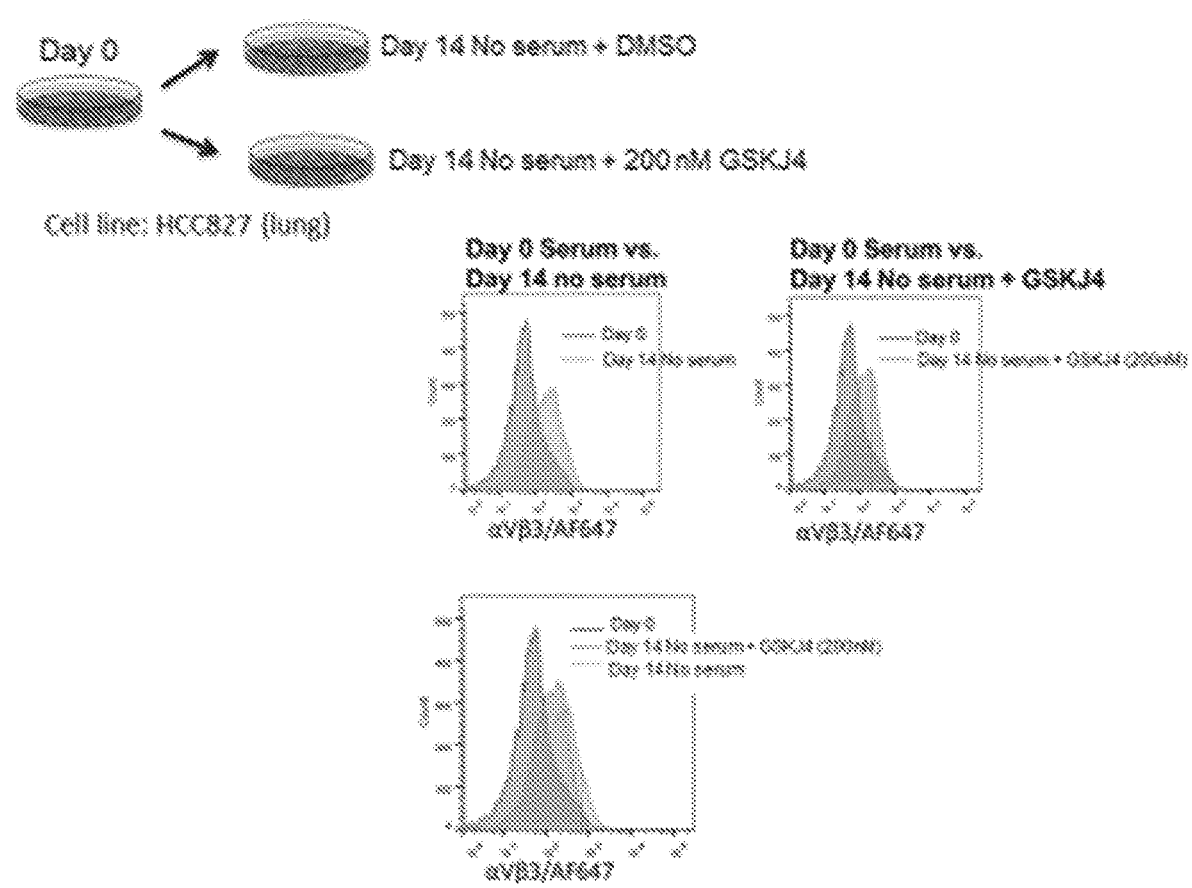
FIG. 14A illustrates the experimental protocol, a 14 day assay for cell surface induction of integrin β3 by nutrient deprivation, and FIG. 14B graphically illustrates images (data from FIG. 13, cell sorting) showing histone demethylase (GSKJ4) prevents the expansion of integrin β3 expressing stem population during nutrient deprivation, as discussed in detail in Example 1, below.

FIG. 14A illustrates the experimental protocol, a 14 day assay for cell surface induction of integrin β3 by nutrient deprivation, and FIG. 14B graphically illustrates images (data from FIG. 13, cell sorting) showing histone demethylase (GSKJ4) prevents the expansion of integrin β3 expressing stem population during nutrient deprivation. The data shows that lung cancer cells (HCC827) treated with JMJD3 histone demethylase inhibitor GSKJ4 prevents the induction of integrin β3 gene expression and formation of the heterodimeric αVβ3 cell surface expression.

A number of exemplary embodiments have been described. Nevertheless, it will be understood that various modifications may be made without departing from the spirit and scope of the invention. Accordingly, other embodiments are within the scope of the following claims.

What is claimed is:

1. A method for treating or ameliorating lung cancer or a lung tumor in an individual in need thereof by slowing or preventing the phenotypic conversion of a lung cancer cell or lung tumor cell that does not express an alpha-V (α-V)/beta-3 (β3) polypeptide dimer to a lung cancer stem cell or lung tumor stem cell phenotype that expresses an alpha-V (α-V)/beta-3 (β3) polypeptide dimer in the individual;

the method comprising:
   (a) identifying the individual has lung cancer or a lung tumor that does not express a cell surface alpha-V (α-V)/beta-3 (β3) polypeptide dimer, and
   (b) administering to the identified individual a pharmaceutical composition comprising GSKJ4 to inhibit or deplete a histone acetyl transferase activity,
   thereby slowing or preventing the phenotypic conversion of the lung cancer cell or lung tumor cell to the lung cancer stem cell or a lung tumor stem cell.

2. The method of claim 1, wherein inhibition or depletion of histone acetyl transferase activity comprises inhibition or depletion of histone acetyl transferase gene or transcript expression activity.

3. The method of claim 1, wherein the inhibition or depletion of histone acetyl transferase activity comprises depletion of histone acetyl transferase protein activity.

4. The method of claim 1, wherein pharmaceutical composition is formulated for in vivo administration to the individual in need thereof.

5. The method of claim 1, wherein pharmaceutical composition is administered to the individual in need thereof intravenously (IV), parenterally, nasally, topically, orally, or by liposome or targeted or vessel-targeted nanoparticle delivery.

\* \* \* \* \*